(12) United States Patent
Chong et al.

(10) Patent No.: US 8,394,840 B2
(45) Date of Patent: Mar. 12, 2013

(54) MODULATORS OF SPERM HYPERMOTILITY AND USES THEREOF

(75) Inventors: Jayhong A. Chong, Brookline, MA (US); Magdalene M. Moran, Brookline, MA (US)

(73) Assignee: Hydra Biosciences, Inc., Cambridge, MA (US)

( * ) Notice: Subject to any disclaimer, the term of this patent is extended or adjusted under 35 U.S.C. 154(b) by 1705 days.

(21) Appl. No.: 11/453,475

(22) Filed: Jun. 15, 2006

(65) Prior Publication Data

US 2007/0004785 A1      Jan. 4, 2007

Related U.S. Application Data

(60) Provisional application No. 60/691,339, filed on Jun. 15, 2005.

(51) Int. Cl.
 A61K 31/41    (2006.01)
 A61K 31/42    (2006.01)
 A61K 31/38    (2006.01)
(52) U.S. Cl. .................. 514/364; 514/379; 514/438
(58) Field of Classification Search .............. 514/364, 514/379, 438
 See application file for complete search history.

(56) References Cited

U.S. PATENT DOCUMENTS

| | | | |
|---|---|---|---|
| 4,957,119 A | 9/1990 | De Nijs | |
| 5,088,505 A | 2/1992 | De Nijs | |
| 5,458,114 A | 10/1995 | Herr | |
| 5,733,565 A | 3/1998 | Moo-Young | |
| 5,935,578 A | 8/1999 | Alves | |
| 2001/0036965 A1 | 11/2001 | Digenis | |
| 2002/0103414 A1 | 8/2002 | Harrison | |
| 2004/0038421 A1 | 2/2004 | Cuppoletti | |
| 2004/0118408 A1 | 6/2004 | Wang | |
| 2004/0157292 A1 | 8/2004 | Clapham | |
| 2004/0163652 A1 | 8/2004 | Watson | |
| 2005/0042249 A1 | 2/2005 | Ahmad | |
| 2005/0076916 A1 | 4/2005 | Barder | |
| 2005/0101767 A1 | 5/2005 | Clapham | |
| 2005/0202539 A1 | 9/2005 | Chong | |
| 2006/0048784 A1 | 3/2006 | Turner | |

FOREIGN PATENT DOCUMENTS

| | | |
|---|---|---|
| EP | 0054872 | 6/1982 |
| WO | WO-94/01422 | 1/1994 |
| WO | WO 01/33219 | 5/2001 |
| WO | WO 01/59446 | 8/2001 |
| WO | WO-02/090567 | 11/2002 |
| WO | WO 03/054141 | 7/2003 |
| WO | WO 2004/015066 | 2/2004 |
| WO | WO 2004/015067 | 2/2004 |

OTHER PUBLICATIONS

Andreichikov et al., "3, 4-Diaroylfuroxane," Database CA, Chemical Abstracts Service from Russian Patent 594,118 (Feb. 25, 1978).
Moharram et al., "Design and Synthesis of 3'- and 5'-O-(3-Benzenesulfonylfuroxan-4-yl)-2'-deoxyuridines: Biological Evaluation as Hybrid Nitric Oxide Donor-Nucleoside Anticancer Agents," J. Med. Chem., 47:1840-1846, (2004).
Sudo et al., "High-throughput screening of low molecular weight NS3-NS4A protease inhibitors using a fluorescence resonance energy transfer substrate," Antiviral Chemistry & Chemotherapy, 16:385-392, (2005).
Takahashi et al., "Preparation of dicarbonyl furoxan derivatives as horticultural and agricultural fungicides," Database CA, Chemical Abstracts Service from Japanese Patent 11240874 (Sep. 7, 1999).
Carlson et al., "CatSper1 required for evoked $CA^{2+}$ entry and control of flagellar function in sperm," PNAS 100(25):14864-14868, (2003).
Gill et al. "Flux Assays in High Throughput Screening of Ion Channels in Drug Discovery," Assay Drug Dev., 1(5):709-717 (2003).
Kirichok et al., "Whole-cell patch-clamp measurements of spermatozoa reveal an alkaline-activated $Ca^{2+}$ channel," Nature, 439:737-40 (2006).
Lobley et al, "Identification of human and mouse CatSper3 and CatSper4 genes: Characterisation of a common interaction domain and evidence for expression in testis," Reproductive Biology Endocrinology, 1:1-15 (2003).
Mortimer et al., "Kinematics of Human Spermatozoa Incubated Under Capacitating Conditions," Journal of Andrology, 11(3):195-203 (1990).
Nikpoor et al., "CatSper gene expression in postnatal development of mouse testis and in subfertile men with deficient sperm motility," Human Reproduction, 19(1):124-128 (2004).
Quill et al., "A voltage-gated ion channel expressed specifically in spermatozoa," PNAS, 98(22):12527-12531 (2001).
Ren et al., "A sperm ion channel required for sperm motility and male fertility," Nature, 413:603-609 (2001).
Ren et al., "Direct Submission," Nature, 413(6856):603-609 (2001).
Schmidt et al., "Induced hyperactivity in boar spermatozoa and its evaluation by computer-assisted sperm analysis," Reproduction, 128:171-179 (2004).
Wennemuth et al., "Bicarbonate actions on flagellar and ca2+-channel responses: initial events in sperm activation," Development, 130:1317-1326 (2003).
Wennemuth et al., "$Ca_v2.2$ and $ca_v2.3$ (N- and R-type) $ca^{2+}$ Channels in Depolarization-evoked Entry of $Ca^{2+}$ into Mouse Sperm," J. Biol. Chem., 275(28):21210-21217 (2000).
Xia et al., "State-dependent inhibition of L-type calcium channels: cell-based assay in high-throughput format," Anal. Biochem., 327(1):74-81 (2004).
Zhang et al., "Association of Catsperi1 or 2 with $Ca_v3.3$ Leads to Suppression of T-Type Calcium Channel Activity," JBC Papers in Press, Published on Jun. 1, 2006 as manuscript M511288200.

*Primary Examiner* — Renee Claytor
(74) *Attorney, Agent, or Firm* — Andrea L. C. Robidoux; Dwight D. Kim; Choate, Hall & Stewart LLP

(57) ABSTRACT

The invention provides novel compositions and compounds that inhibit CatSper channel activity, that preferentially inhibits sperm hyperactivity over sperm motility, or both. The compounds of the invention are useful as contraceptive agents that may be adminstered to males, females, or concurrently to both sexual partners. The invention further provides methods of conducting drug discovery business and of conducting a reproductive medicine business. The invention also provides methods of identifying compounds that modulate sperm hypermotility.

6 Claims, 25 Drawing Sheets

Forward Progressive

Hyperactivated

Screen bacteria expressing
CatSper with library of compounds

↓

Identify CatSper Channel Modulators

↓

Test blockers *in vivo* on human sperm

↓

Classify blockers according to
effects on motility/hypermotility

| Effect of Compound on (Hyperactivation/Motility) | | |
|---|---|---|
| (+/+) | (+/0) | (+/-) |
| (0/+) | (0/0) | (0/-) |
| (-/+) | (-/0) | (-/-) |

↓

┄┄▶ Identified related compounds

↓

┄┄┄ Test related compounds
on human sperm

Fig. 4

| Compound-No | 1st | 2nd |
|---|---|---|
| 827.0 | | |
| 584.234 | | |
| 175.0 | X | |
| 373.3 | | |
| 437.0 | | + |
| 552.0 | + | |
| 701.0 | | |
| 694.0 | X | |
| 067.0 | | + |
| 422.0 | | |
| 058.23 | X | |
| 562.0 | | |
| 939.0 | | |
| 877.0 | X | |
| 424.239 | | |
| 544.0 | | |
| 770.0 | | + |
| 962.0 | | + |
| 923.0 | + | |
| 075.5 | | |

| Comp-No | 1st | 2nd |
|---|---|---|
| 244.0 | + | |
| 478.0 | | |
| 424.117 | | |
| 424.169 | | |
| 535.0 | | |
| 182.1 | | |
| 006.0 | | |
| 370.0 | + | |
| 662.0 | | |
| 273.0 | | |
| 782.0 | | |
| 178.0 | + | |
| 756.0 | | X |
| 585.0 | | |
| 234.0 | | |
| 095.0 | | |
| 732.0 | | |
| 806.0 | | |
| 580.0 | | |
| 640.0 | | |

| Comp-No | 1st | 2nd |
|---|---|---|
| 424.155 | + | + |
| 176.0 | X | |
| 496.0 | + | |
| 287.0 | + | |
| 557.0 | + | + |
| 738.0 | X | X |
| 133.0 | | |
| 858.0 | | |
| 329.0 | | |
| 422.0 | | |
| 083.0 | + | + |
| 480.0 | + | + |
| 080.0 | + | + |
| 136.0 | + | |
| 686.17 | + | |
| 558.0 | | |
| 554.0 | | |
| 545.0 | + | + |
| 973.0 | | |
| 418.0 | | |

| Comp-No | 1st | 2nd |
|---|---|---|
| 543.0 | | |
| 432.0 | + | |
| 859.0 | | |
| 542.0 | + | |
| 210.0 | | |
| 046.0 | | X |
| 835.0 | | |
| 897.0 | | |
| 744.0 | | |
| 848.0 | | |
| 754.0 | + | X |
| 647.0 | | |
| 547.0 | | |
| 510.0 | | |
| 193.0 | | |
| 060.0 | | |
| 850.0 | | |
| 582.0 | + | + |
| 350.0 | | |
| 581.0 | | |

| Comp-No | 1st | 2nd |
|---|---|---|
| 163.0 | | |
| 245.0 | | |
| 279.0 | X | |
| 029.0 | | |
| 787.0 | X | |
| 441.0 | | |
| 028.0 | | |
| 440.0 | | |
| 202.0 | | X |

Compound 738

Compound 354

Elements for Specific Inhibition of Hyperactivation

| | |
|---|---|
| 1 | Permanently charged N-O group |
| 2 | Carbonyl oxygen |
| 3 | Large planar group |
| 4 | Bilateral symmetry |

Inactive

Active

Inactive

Active

Inactive

Active

Inactive

Inactive

MODULATORS OF SPERM HYPERMOTILITY AND USES THEREOF

CROSS-REFERENCE TO RELATED APPLICATIONS

This application claims the benefit of the filing date of U.S. application No. 60/691,339, filed Jun. 15, 2005, entitled "MODULATORS OF CATSPER CHANNEL FUNCTION AND USES THEREOF." The entire teachings of the referenced application is incorporated by reference herein.

FIELD OF THE INVENTION

The field of this invention is mammalian fertility.

BACKGROUND OF THE INVENTION

Several family planning strategies are currently widespread in the United States including sterilization, abstinence, abortion and contraception. Of these four birth control methods, contraception is the most widely utilized. Oral contraceptives and barrier methods are popular and efficacious but have significant shortcomings. Currently available oral contraceptives modulate hormone levels and are documented to be associated with nausea, headaches, breast tenderness, weight gain, irregular bleeding, mood changes, and more significant side effects including increased risks of cardiovascular disease and breast cancer, especially in women over 35. Currently available oral contraceptives may also lead to adverse cross reactions with other drugs, including cyclosporine, dantrolene and warfarin. Furthermore, currently available oral contraceptives lose efficacy when combined with antibiotics. Barrier methods, while safe, have failure rates approaching 20%. Other less common contraceptive methods, such as immunization of women against sperm polypeptides (see U.S. Pat. No. 5,935,578), may result in irreversible immunity to sperm and permanent reduction in fertility. There is a clear need for increased availability of and improvements in contraceptives that offer superior safety, efficacy, convenience, acceptability, affordability and reversibility.

A $Ca^{+2}$ channel, CatSper1, has recently been cloned (see U.S. Patent Pub No. 2004/0157292). CatSper1 is naturally expressed exclusively in the testis and not in other tissues such as the brain, heart, kidney or the immune system. Targeted disruption of the gene results in male sterility in otherwise normal mice. Sperm hyperactivity in CatSper1−/− (knockout) mice is dramatically decreased, and cyclic AMP induced $Ca^{+2}$ influx is abolished in the sperm of mutant mice.

The invention provides novel agents that inhibit sperm hyperactivity. In one embodiment, the novel agents are antagonists of the CatSper1 channel which specifically inhibit sperm hyperactivity. The restricted expression of CatSper1 and its essential role in fertility make the CatSper1 channel antagonists promising contraceptive agents with high potency and decreased side effects.

SUMMARY OF THE INVENTION

One aspect of the invention provides a composition comprising (i) a pharmaceutically-acceptable carrier and (ii) a compound, or a pharmaceutically acceptable salt thereof, which preferentially inhibits sperm hyperactivity over sperm motility/viability. Another aspect of the invention provides a composition comprising (i) a pharmaceutically-acceptable carrier and (ii) a compound, or a pharmaceutically acceptable salt thereof, which inhibits CatSper channel activity. Another aspect of the invention provides a composition comprising (i) a pharmaceutically-acceptable carrier and (ii) a compound, or a pharmaceutically acceptable salt thereof, which inhibits the activity of a CatSper1-containing channel. Another aspect of the invention provides a composition comprising (i) a pharmaceutically-acceptable carrier and (ii) a compound, or a pharmaceutically acceptable salt thereof, which inhibits the activity of a CatSper1-containing channel and which preferentially inhibits sperm hyperactivity over sperm motility/viability. In one embodiment, the compositions are pharmaceutical compositions.

In one embodiment of the compositions provided herein, the compound is represented by the formula:

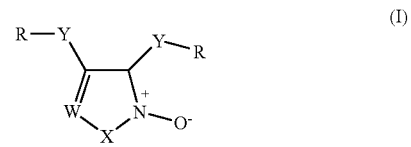

(I)

wherein W is CR' or N, wherein R' is a lower alkyl or a hydrogen; X is O or S; Y, independently for each occurrence, is C=O, C=S, or $SO_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl, or a pharmaceutically acceptable salt thereof.

In certain embodiments, W is N. In certain embodiments, X is O. In certain embodiments, Y is C=O. In certain embodiments, R' is H. In certain embodiments, the two Y—R substituents are identical. In certain embodiments, R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl.

In certain embodiments, the compound is

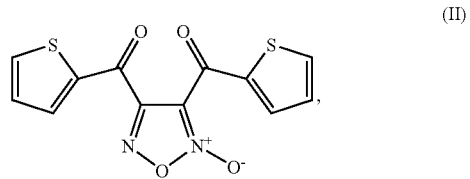

(II)

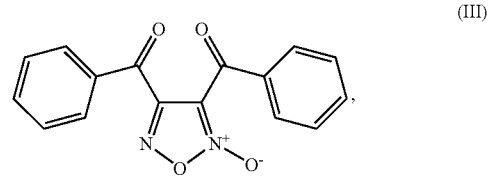

(III)

(IV)

-continued

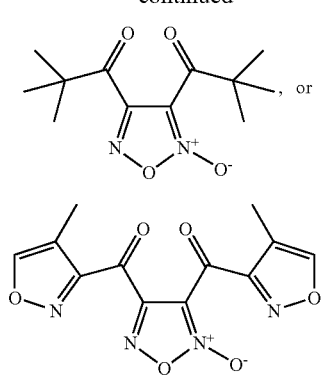

or a pharmaceutically acceptable salt thereof.

In some embodiments, the composition is a pharmaceutical composition. In some embodiments, the composition comprises at least one additional contraceptive agent. Contraceptive agents include, but are not limited to, norgestimate (NGM), ethinyl estradiol (EE) and 17-β estradiol (E2), norethindrone, norethindrone acetate, chlormadione acetate, norethynodrel, norgestrel, medroxyprogesterone acetate, megeskol acetate, lynestrenol, quingeskone, ethynodiol acetate, and dimethisterone. In some embodiments, the composition comprises an anti-erectile dysfunction agent. Anti-erectile dysfunction agents include, but are not limited to, vascular smooth muscle relaxants, α- adrenoceptor antagonists, and male hormones. In some embodiments, the composition is formulated as an injection, a transdermal patch, a bioerodable implant, a lubricant, a moisturizer, a foam, a jelly, or a sponge.

Another aspect of the invention provides a composition comprising (i) a pharmaceutically-acceptable carrier and (ii) a compound, or a pharmaceutically acceptable salt thereof, wherein the compound competes for binding to a CatSper1 channel with the CatSper1 channel modulator represented the formula (I), or any one of formulas (II)-(VI).

Another aspect of the invention provides a method of decreasing CatSper1 channel activity in a cell, such as in a spermatozoon, the method comprising contacting the cell with a compound represented the formula (I), or any one of formulas (II)-(VI).

A related aspect of the invention provides a method of decreasing $Ca^{+2}$ influx into a cell, such as in a spermatozoon, the method comprising contacting the cell with a compound represented by formula (I), or any one of formulas (II)-(VI).

Another aspect of the invention provides a method of selectively decreasing the hyperactivity of a spermatozoon, the method comprising contacting the spermatozoon with a compound represented by formula (I), or any one of formulas (II)-(VI).

Another aspect of the invention provides a method of decreasing the fertility of a male subject comprising administering to the male a compound which (i) decreases CatSper1 channel activity; (ii) preferentially inhibits sperm hyperactivity over sperm motility/viability; or (iii) both. A related aspect of the invention provides a method of causing reversible infertility in a male subject comprising administering to said male a compound which (i) decreases CatSper1 channel activity; (ii) preferentially inhibits sperm hyperactivity over sperm motility/viability; or (iii) both. Another related aspect of the invention provides a method of contraception comprising: administering to a male subject a compound which (i) decreases CatSper1 channel activity; (ii) preferentially inhibits sperm hyperactivity over sperm motility/viability; or (iii) both. Yet another related aspect of the invention provides a method of contraception comprising: administering to a female subject a compound which (i) decreases CatSper1 channel activity; (ii) preferentially inhibits sperm hyperactivity over sperm motility/viability; or (iii) both.

In one embodiment, the compound that decreases CatSper1 channel activity (i) is represented by any one of formulas (I)-(VI); or (ii) competes for binding to the CatSper1 channel with a compound represented by formula (I)-(VI). In some embodiments, the compound is in a formulation selected from an injection, a transdermal patch, a bioerodable implant, a lubricant, a moisturizer, a foam, a jelly, and a sponge. In one embodiment, the compound is administered into at least one of the vagina, uterus and fallopian tubes of said female.

Another aspect of the invention provides a method of decreasing the joint fertility between a male and a female subject, the method comprising administering to the male and to the female a compound which inhibits sperm hyperactivity. In one embodiment, the compound is represented by formula (I), or any one of formulas (II)-(VI). In one embodiment, the compound is an inhibitor of a CatSper channel. In another embodiment, the CatSper channel is a CatSper1 channel.

In one embodiment, the compound is not an antibody or an antigen-binding fragment thereof. In another embodiment, the compound is not (i) an antibody or an antigen-binding fragment thereof, (ii) an antibody or an antigen-binding fragment thereof which specifically binds a CatSper channel; or (i) an antibody or an antigen-binding fragment thereof that specifically binds a CatSper1 channel. In one embodiment, the compound is not a polypeptide. In another embodiment, the compound lacks any peptide and/or saccharide linkages. In another embodiment, the compound has less than 4, 3 or 2 peptide and/or saccharide linkages.

In one embodiment, the compound is not an nucleic acid, such as an siRNA, a hairpin RNA or double stranded RNA. In one embodiment, the compound is not an antisense nucleic acid or a nucleic acid capable of inhibiting the expression of a CatSper gene, or a CatSper1 gene, by RNA interference. In another embodiment, the compound is not (i) a nucleic acid, (ii) a nucleic acid capable of hybridizing to a CatSper nucleic acid under high or low hybridization conditions; or (iii) a nucleic acid capable of hybridizing to a CatSper1 nucleic acid under high or low hybridization conditions. In one embodiment, the compound does not decrease the mRNA levels of a CatSper gene, or of a CatSper1 gene, in a spermatozoon that is contacted with the compound.

Another aspect of the invention provides the use of a compound which decreases CatSper1 channel activity in the manufacture of a medicament for decreasing the fertility of a male subject. Another aspect of the invention provides the use of a compound which decreases CatSper1 channel activity in the manufacture of a medicament for causing reversible infertility in a male subject. Another aspect of the invention provides the use of a compound which decreases CatSper1 channel activity in the manufacture of a medicament for contraception in a male subject. Another aspect of the invention provides the use of a compound which decreases CatSper1 channel activity in the manufacture of a medicament for causing reversible infertility in a female subject. In one embodiment, the compound is represented by formula (I), or any one of formulas (II)-(VI). In one embodiment, the compound is in a formulation selected from the group consisting of an injection, a transdermal patch, a bioerodable implant, a lubricant, a moisturizer, a foam, a jelly, and a sponge. In one embodiment, said compound preferentially inhibits sperm hyperactivity over sperm motility. In another embodiment, the compound is suitable for administration into at least one of the vagina, uterus and fallopian tubes of said female.

Another aspect of the invention provides the use method of increasing the fertility of a male subject having excessive spermatozoa hyperactivity, the method comprising administering to the male subject a therapeutically effective amount of any of the compositions described herein. A related aspect of the invention provides the use method of increasing fertility in a female inseminated with spermatozoa having excessive hyperactivity, the method comprising administering to the female subject a therapeutically effective amount of the composition provided herein. The composition may be administered to the female subject prior to, concurrent to, or after insemination.

Another aspect of the invention provides a method of conducting a drug discovery business comprising: (a) identifying one or more agents which antagonize CatSper1 channel activity; (b) determining if an agent identified in step (a), or an analog thereof, inhibits spermatozoon hyperactivity; (c) conducting therapeutic profiling of an agent identified as an inhibitor of hyperactivity (b) for efficacy and toxicity in one or more animal models; and (d) formulating a pharmaceutical preparation including one or more agents identified in step (c) as having an acceptable therapeutic profile. Certain embodiments further include the step of establishing a system for distributing the pharmaceutical preparation for sale, and optionally including establishing a sales group for marketing the pharmaceutical preparation.

Another aspect of the invention provides a method of conducting a reproductive medicine business comprising: (a) examining a spermatozoon sample from a male patient, wherein said patient is experiencing a fertility problem; (b) determining if said spermatozoon are characterized by excessive hyperactivity; (c) performing in vitro analysis to determine the efficacy of a CatSper1 channel antagonist in decreasing excessive hyperactivity; and (d) establishing a treatment regimen comprising administering an amount of a CatSper1 channel antagonist effective to decrease excessive hyperactivity in said male. Certain embodiments further include a step wherein said male is monitored by a physician to evaluate improvement in fertility. Certain embodiments further include a step of billing the patient or the patient's health care provider.

Another aspect of the invention provides a method of identifying a compound that inhibits sperm hyperactivation, the method comprising: (a) identifying a compound that inhibits CatSper channel activity; and (b) determining if the compound identified in step (a) inhibits sperm hyperactivation. A related aspect of the invention provides a method of identifying a compound that promotes sperm hyperactivation, the method comprising: (a) identifying a compound that inhibits CatSper channel activity; and (b) determining if the compound identified in step (a) promotes sperm hyperactivation. Another related aspect of the invention provides a method of identifying a compound that inhibits sperm hyperactivation, the method comprising: (a) identifying a compound that activates CatSper channel activity; and (b) determining if the compound identified in step (a) inhibits sperm hyperactivation. Another related aspect of the invention provides a method of identifying a compound that promotes sperm hyperactivation, the method comprising: (a) identifying a compound that inhibits CatSper channel activity; and (b) determining if the compound identified in step (a) promotes sperm hyperactivation. In one embodiment, the compound is a small molecule. In another embodiment, the CatSper channel activity is CatSper1 channel activity. In yet another embodiment, step (b) comprises: determining if the compound identified in step (a) inhibits sperm hyperactivation relative to inhibiting sperm motility or relative to inhibiting sperm viability.

BRIEF DESCRIPTION OF THE DRAWINGS

FIG. 2 shows a general strategy for the identification of modulators of CatSper channel activity and modulators of sperm motility and hyperactivity.

FIG. 4 shows experimental results of testing 89 compounds in duplicate for their effects on sperm motility and hyperactivity ex vivo.

FIG. 16 additionally provides another compound that did not specifically inhibit sperm hyperactivity (bottom panel).

DETAILED DESCRIPTION OF THE INVENTION

I. Overview

Figure 1:
FIG. 1 shows a schematic representation of normal motility, or "forward progressive" movement (upper panel) relative to hyperactivity (hyperactivated or hyperactivated movement; lower panel). This figure is adapted from FIG. 1 of Mortimer and Mortimer, (1990) "Kinematics of human spermatozoa incubated under capacitating conditions" *Journal of Andrology*, Vol 11, Issue 3 195-203. The lower panel depicts one exemplary type of hyperactive sperm movement referred to as star-spin. Star-spin, however, is just one non-limiting example of a type of hyperactive sperm movement. Further exemplary hyperactive sperm movements, characteristics, and behaviors are described in Mortimer and Mortimer (1990), which is hereby incorporated by reference in it entirety.
Figure 1:
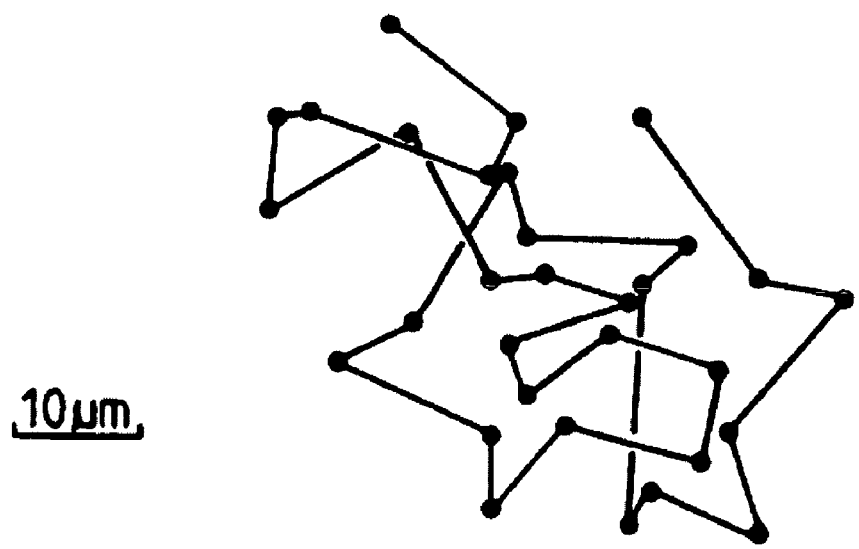

The invention provides, in part, novel modulators of sperm hyperactivation and novel modulators of Cation Channel Sperm-Associated 1 (CatSper1) channel activity, including inhibitors. The invention further provides compositions, and in particular pharmaceutical compositions, comprising the novel inhibitors. The invention also provides uses of these compositions. The compositions of the invention optionally include contraceptive, fertility, or erectile dysfunction medicaments, depending on their intended use. The invention further provides compositions comprising compounds that compete with inhibitors of CatSper1 channel function for binding to the CatSper1 channel. Such compounds may be useful as modulators of CatSper1 channel function, as modulators of sperm hyperactivity, and/or as modulators of fertility in both males and females. The compounds may also be used in in vitro fertilization or in artificial insemination when the spermatozoa are hypermotile or in spermatozoa having excessive CatSper 1 activity.

The invention is based, in part, on applicants' discovery of novel modulators of CatSper1 channel activity which also inhibit the hyperactivation of human sperm. Hyperactivation is an essential step in the fertilization process, making the compounds of the invention attractive contraceptive agents. This is supported by the finding that CatSper1−/−mutant sperm are unable to fertilize ova. Furthermore, the restricted localization of CatSper1 to mature sperm suggests that a specific blocker should not affect other tissues when administered to a male, and thus side effects should be low or nonexistent. Similarly, females would be expected to show few or no side effects from specific inhibitors of CatSper1−/−, whether from inhibitors that are directly administered to the female or from contacting male bodily fluids containing them.

The invention further provides methods of decreasing CatSper1 channel activity in a cell, of decreasing $Ca^{+2}$ influx into a cell, such as in a spermatozoon, by using the compositions described herein. Methods of using these compositions for selectively decreasing the hyperactivity of a spermatozoon are also provided. The cell or spermatozoon may be in a mammal, such as a human. The human may be a male or a female.

The invention further provides methods of modulating fertility, and methods of causing reversible infertility, in a male or a female. Some methods comprise administering compounds that (i) decrease CatSper1 channel activity; (ii) preferentially inhibit sperm hyperactivity over sperm motility and/or viability; or (iii) both. The compounds may be formulated into injectable compositions, transdermal patches, bioerodable implants, lubricants, moisturizers, foams, jellies, sponges, female condoms and the like, for administration to women, or into condoms, implantable devices or penile caps for men. The compounds of the inventions may also be jointly administered to both sexual partners. Such administration is expected to result in constant exposure of the sperm to the compound, both prior to ejaculation while they are in the male and post ejaculation when they are in the female.

The invention also provides methods of screening compounds to identity modulators of sperm hyperactivity. One such method comprises (a) identifying a compound that modulates CatSper channel activity; and (b) determining if the compound identified in step (a) modulates sperm hyperactivation, and optionally determining if it modulates sperm motility and/or sperm viability. In preferred embodiments, the CatSper channel is a CatSper1 channel.

The invention also provides methods of conducting businesses. One aspect provides methods of conducting drug discovery businesses that include (a) identifying one or more agents which modulate CatSper channel activity, preferably CatSper1 activity; and (b) determining if the agent identified in step (a), or an analog thereof, inhibits spermatozoon hyperactivity. The invention also provides a method of conducting a reproductive medicine business that includes (a) examining the spermatozoa sample from a male patient experiencing a fertility problem; (b) determining if said spermatozoon are characterized by altered hyperactivity; (c) performing in vitro analysis to determine the efficacy of a CatSper1 channel modulator in restoring normal hyperactivity; and (d) establishing a treatment regimen comprising administering an amount of a CatSper1 channel modulator effective to restore normal hyperactivity in said male spermatozoa.

II. Definitions

The term "CatSper1 protein" means a sperm-specific cation channel such as the human CatSper1 protein disclosed in U.S. Patent Publication No. 2004/0157292 as SEQ ID NO:2, human allelic variants of the disclosed CatSper1 protein, mammalian homologs of these human CatSper1 proteins, and functional equivalents thereof. CatSper1 is also known as Cation Channel Sperm-Associated 1. The cDNA sequence of CatSper1, is disclosed in U.S. Publication No. 2004/0157292, hereby incorporated by reference in its entirety. Human CatSper1 sequences are also described in public sequence databases, such as Genbank Accession No. NP_444282 and AF407332 (polypeptides) and NM_053054 (mRNA), and in scientific publications (e.g. Ren et al. (2001) Nature 413: 603-609). In one embodiment, allelic variants of a CatSper1 protein have less than 10, 9, 8, 7, 6, 5, 4, 3, 2 or 1 amino acid changes from the amino acid sequence set forth in SEQ ID NO:2 of 2004/0157292.

The term CatSper1 protein refers to naturally occurring proteins as isolated from sperm, recombinantly produced proteins from cells transformed with CatSper1 genes, and fusion proteins in which CatSper1 sequences are fused to N-terminal or C-terminal polypeptides. The term "fragment" refers to fragments of the CatSper1 proteins, such as structural domains and epitopes. A fragment of a CatSper1 protein comprises at least six amino acid residues.

A "CatSper1 channel" refers to a channel comprising a CatSper1 protein. A CatSper1 channel may additionally comprise other polypeptide components, including other channel forming-subunits or regulatory/auxiliary subunits. In some embodiments, a CatSper1 channel is comprised of a homotetramer of CatSper1 subunits. In certain embodiments, the CatSper1 Channel is comprised of one CatSper1 subunit and three additional subunits selected, independently, from CatSper2, CatSper3 and CatSper4. In other embodiments, the CatSper1 Channel is comprised of two CatSper1 subunits and two additional subunits selected, independently, from CatSper2, CatSper3 and CatSper4. In other embodiments, the CatSper1 Channel is comprised of three CatSper1 subunits and an additional subunit selected from CatSper2, CatSper3 and CatSper4. CatSper2 mammalian sequences are described in WO03/054141, CatSper3 sequences in WO04/015067 and CatSper4 in WO04/015066.

As used herein "CatSper Channel" or "CatSper channel" are used interchangeably to refer to a channel comprising at least one CatSper protein (e.g., CatSper1, CatSper2, CatSper3, CatSper4). The CatSper channel may additionally comprise other polypeptide components, including other channel forming subunits or regulatory/auxiliary subunits. In some embodiments, a CatSper channel is comprised of a homotetramer of CatSper subunits (e.g., a homotetramer of CatSper1, CatSper2, CatSper3, or CatSper4 subunits). In certain embodiments, the CatSper Channel is comprised of four subunits, independently selected from CatSper1, CatSper2, CatSper3, or CatSper4. In certain embodiments, the CatSper Channel does not contain a CatSper1 subunit.

As used herein "CatSper1 activity" means any normal biological activity of a wild-type CatSper1 protein when expressed in a cell or cell type in which CatSper1 is normally expressed and under conditions under which CatSper1 is normally expressed. Such activity may include induction of an ion current; mediation of cAMP-induced Ca influx; restoration of sperm motility when expressed in CatSper1−/− sperm; and/or restoration of the ability to penetrate eggs when expressed in CatSper1−/−sperm. CatSper1 channel activity can be measured in sperm cells or spermatocytes, or in other cells in which any necessary accessory factors are present. In certain embodiments, CatSper1 channel activity includes the ability to mediate ion flux when ectopically expressed in a non-sperm cell, for example in a bacterial cell or in a mammalian cell other than a sperm cell.

As used herein "CatSper activity" means any normal biological activity of a wild-type CatSper protein when expressed in a cell or cell type in which CatSper is normally expressed and under conditions under which CatSper is normally expressed. Such activity may include induction of an ion current; mediation of cAMP-induced Ca influx; restoration of sperm motility when expressed in CatSper −/−sperm; and/or restoration of the ability to penetrate eggs when expressed in CatSper −/−sperm. CatSper activity can be measured in sperm cells or spermatocytes, or in other cells in which any necessary accessory factors are present. In certain embodiments, CatSper activity includes the ability to mediate ion flux when ectopically expressed in a non-sperm cell, for example in a bacterial cell or in a mammalian cell other than a sperm cell.

As used herein, the term "effective amount" of an agonist or antagonist, or an enhancer or repressor, means the total amount of the active component(s) of a composition that is sufficient to cause a statistically significant change on a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "sperm motility" refers to the rate of displacement of sperm in fluid medium.

As used herein, the term "sperm hyperactivity" refers to a sperm behavioral state, which naturally occurs during sperm capacitation, typically characterized by high speed (VCL), low linearity (LIN) and exaggerated lateral head movement (ALH). Sperm hyperactivity may be measured using automated methods (see for Schmidt H et al. (2004) *Reproduction;* 128(2):171-9. FIG. 1 is a representative diagram of one type of behavior observed in hyperactivated sperm (bottom panel) relative to nonhyperactive sperm (upper panel). This particular, non-limiting example of hyperactive sperm behavior is referred to as star-spin. Other patterns and characteristics of hyperactive sperm are provided in Mortimer and Mortimer (1990) *Journal of Andrology*, Vol 11, Issue 3, pages 195-203, which is hereby incorporated by reference in its entirety.

The phrase "therapeutically effective amount" as used herein means that amount of an agent or composition which is effective for producing some desired therapeutic effect. Optionally, the therapeutically effective amount is that amount of an agent or composition which is effective for producing some desired therapeutic effect at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, the pharmaceutical preparation is non-pyrogenic, i.e., does not elevate the body temperature of a patient.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977), J. Pharm. Sci. 66: 1-19).

The terms "antagonist" and "inhibitor" are used interchangeable to refer to an agent that inhibits or suppresses a biological activity, such as to repress activity of an ion channel, such as a CatSper1 Channel or a CatSper Channel.

The term "preventing" is art-recognized, and when used in relation to a condition, such as fertilization or pregnancy, a disease such as cancer, a syndrome complex such as heart failure or any other medical condition, is well understood in the art, and includes administration of a composition which reduces the frequency of a medical condition in a subject relative to a subject which does not receive the composition, e.g., by a statistically and/or clinically significant amount.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The terms "compound" and "agent" are used interchangeably to refer to the inhibitors/antagonists of the invention. In certain embodiments, the compounds are small organic or inorganic molecules, e.g., with molecular weights less than 7500 amu, preferably less than 5000 amu, and even more preferably less than 2000, 1500, 1000, or 500 amu. One class of small organic or inorganic molecules are non-peptidyl, e.g., containing 2, 1, or no peptide and/or saccharide linkages.

The term "acylamino" is art-recognized and refers to a moiety that can be represented by the general formula:

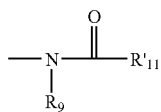

wherein $R_9$ is as defined above, and $R'_{11}$ represents a hydrogen, an alkyl, an alkenyl or $-(CH_2)_m-R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m-R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

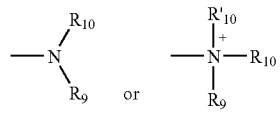

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

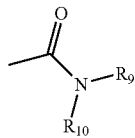

wherein $R_9$, $R_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

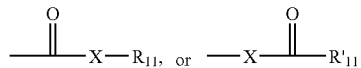

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocyclyl, aryl, heteroaryl, cycloalkylalkyl, heterocyclylalkyl, aralkyl, or heteroaralkyl, any of which may itself be further substituted), as well as halogen, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, and phosphoryl. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

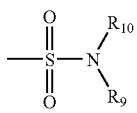

in which $R_9$ and $R_{10}$ are as defined above.

The term "sulfate" is art recognized and includes a moiety that can be represented by the general formula:

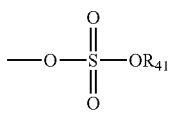

in which $R_{41}$ is as defined above.

The term "sulfonamido" is art recognized and includes a moiety that can be represented by the general formula:

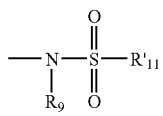

in which $R_9$ and $R'_{11}$ are as defined above.

The term "sulfonate" is art-recognized and includes a moiety that can be represented by the general formula::

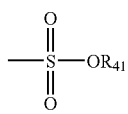

in which $R_{41}$ is an electron pair, hydrogen, alkyl, cycloalkyl, or aryl.

The terms "sulfoxido" or "sulfinyl", as used herein, refers to a moiety that can be represented by the general formula:

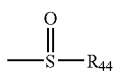

in which $R_{44}$ is selected from the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit CatSper channel activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Compositions

One aspect of the invention provides novel compositions. In one embodiment, the compositions are pharmaceutical compositions. One aspect of the invention provides a composition comprising (i) a pharmaceutically-acceptable carrier and (ii) a compound, or a pharmaceutically acceptable salt thereof, which preferentially inhibits sperm hyperactivity over sperm motility. By preferential inhibition of hyperactivity over sperm motility, it is meant that the $IC_{50}$ for inhibition of hyperactivity is at least 1.5, 2, 3, 4, 5, 6, 7, 8, 9, 10, 15, 20, 25, 30, 35, 40, 45, 50, 60, 70, 80, 90, 100, 200, 500, 1000, 2000, 5000 or 10000 times lower than the $IC_{50}$ for inhibition of sperm motility. In a specific embodiment, the $IC_{50}$ for inhibition of hyperactivity is at least 10 times lower than the $IC_{50}$ for inhibition of sperm motility. In a specific embodiment, the $IC_{50}$ for inhibition of hyperactivity is at least 100 times lower than the $IC_{50}$ for inhibition of sperm motility. In a specific embodiment, the $IC_{50}$ for inhibition of hyperactivity is at least 1000 times lower than the $IC_{50}$ for inhibition of sperm motility.

One aspect of the invention provides a composition comprising (i) a pharmaceutically-acceptable carrier and (ii) a compound, or a pharmaceutically acceptable salt thereof, which preferentially inhibits sperm hyperactivity over sperm viability. By preferential inhibition of sperm hyperactivity over sperm viability, it is meant that the $IC_{50}$ for inhibition of hyperactivity is at least 1.5, 2, 3, 4, 5, 6, 7, 8, 9, 10, 15, 20, 25, 30, 35, 40, 45, 50, 60, 70, 80, 90, 100, 200, 500, 1000, 2000, 5000 or 10000 times lower than the $IC_{50}$ for inhibition of sperm viability/inducing apoptosis. In a specific embodiment, the $IC_{50}$ for inhibition of hyperactivity is at least 10 times lower than the $IC_{50}$ for inhibition of sperm viability or for inducing apoptosis. In a specific embodiment, the $IC_{50}$ for inhibition of hyperactivity is at least 100 times lower than the $IC_{50}$ for inhibition of sperm viability/inducing apoptosis. In a specific embodiment, the $IC_{50}$ for inhibition of hyperactivity is at least 1000 times lower than the $IC_{50}$ for inhibition of sperm viability/inducing apoptosis.

Another aspect of the invention provides a composition comprising (i) a pharmaceutically-acceptable carrier and (ii) a compound, or a pharmaceutically acceptable salt thereof, which preferentially inhibits sperm hyperactivity over both sperm motility and sperm viability. By preferential inhibition, it is meant that the $IC_{50}$ for inhibition of hyperactivity is at least 1.5, 2, 3, 4, 5, 6, 7, 8, 9, 10, 15, 20, 25, 30, 35, 40, 45, 50, 60, 70, 80, 90, 100, 200, 500, 1000, 2000, 5000 or 10000 times lower than the $IC_{50}$ for inhibition of sperm motility and sperm viability/apoptosis induction. In a specific embodiment, the $IC_{50}$ for inhibition of hyperactivity is at least 10 times lower than the $IC_{50}$ for inhibition of sperm motility and sperm viability. In a specific embodiment, the $IC_{50}$ for inhibition of hyperactivity is at least 100 times lower than the $IC_{50}$ for inhibition of sperm motility and sperm viability/apoptosis induction. In a specific embodiment, the $IC_{50}$ for inhibition of hyperactivity is at least 1000 times lower than the $IC_{50}$ for inhibition of sperm motility and sperm viability. In any of the foregoing embodiments of this aspect of the invention, it is recognized that although the compounds preferentially inhibit sperm hyperactivity over both sperm motility and sperm viability, the $IC_{50}$ for sperm motility and sperm viability is not necessarily the same.

Another aspect of the invention provides a composition comprising (i) a pharmaceutically-acceptable carrier and (ii) a compound, or a pharmaceutically acceptable salt thereof, which inhibits CatSper1 channel activity. A related aspect of the invention provides a composition comprising (i) a pharmaceutically-acceptable carrier and (ii) a compound, or a pharmaceutically acceptable salt thereof, which inhibits the activity of a CatSper1-containing channel and which preferentially inhibits sperm hyperactivity over sperm motility. In particular embodiments, the compound is more selective for CatSper1 channel activity than for the activity of other $Ca^{+2}$ channels, e.g., 10-fold, and more preferably at least 100- or even 1000-fold more selective than for mammalian voltage-gated $Ca^{+2}$ channels, such as Ca(V)3.2, or for the human HERG channel.

In other embodiments, the differential is smaller, e.g., it more strongly inhibits CatSper1 channel activity than that of mammalian voltage-gated $Ca^{+2}$ channels, such as Ca(V)3.2, or the human HERG channel, preferably at least twice, three times, five times, or even ten times more strongly. Such comparisons may be made, for example, by comparing $IC_{50}$ values.

In certain embodiments, a compound which is an antagonist of CatSper1 channel activity selectively antagonizes CatSper1 channel activity over other ion channel activities, e.g., the compound modulates the activity of CatSper1 channel at least an order of magnitude more strongly than it modulates the activity of Ca(V)3.2 or the human HERG channel, preferably at least two orders of magnitude more strongly, even more preferably at least three orders of magnitude more strongly. Such comparisons may be made, for example, by comparing $IC_{50}$ values.

Similarly, in particular embodiments, the compound lacks significant activity against one or more targets other than a CatSper channel. For example, the compound may have an $IC_{50}$ above 100 nM, above 1 µM, 10 µM or even 100 µM for inhibiting one or more of Ca(V)3.2 and the human HERG channel.

Yet another aspect of the invention provides a composition comprising (i) a pharmaceutically-acceptable carrier and (ii) a compound, or a pharmaceutically acceptable salt thereof, represented by the formula:

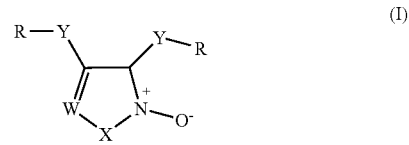

(I)

wherein W is CR' or N; R' is a lower alkyl or a hydrogen; X is O or S; Y, independently for each occurrence, is C=O, C=S, or $SO_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl. In one embodiment, W is N. In another embodiment, X is O. In another embodiment, Y is C=O. In another embodiment, R is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl.

In one specific embodiment, the compound is represent by formula:

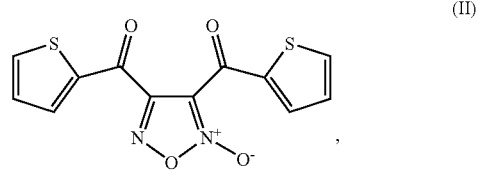 [SMILES: O=C(c1cccs1)c1no[n+]([O-])c1C(=O)c1cccs1]

(II)

or a pharmaceutically acceptable salt thereof.

In another embodiment, the compound is represent by formula:

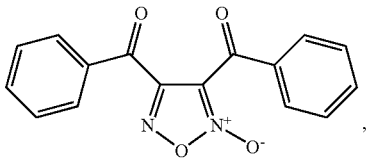   (III)

or a pharmaceutically acceptable salt thereof.

In another embodiment, the compound is represent by formula:

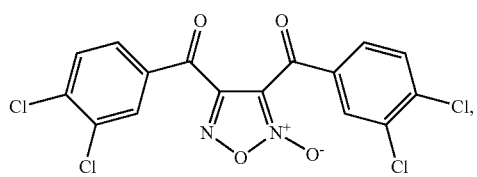   (IV)

or a pharmaceutically acceptable salt thereof.

In another embodiment, the compound is represent by formula:

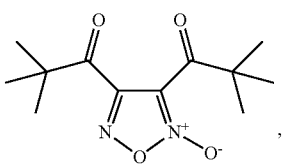   (V)

or a pharmaceutically acceptable salt thereof.

In another embodiment, the compound is represent by formula:

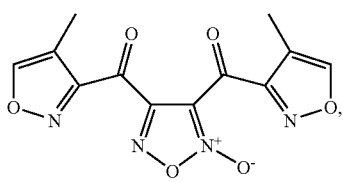   (VI)

or a pharmaceutically acceptable salt thereof.

The invention also provides a composition comprising (i) a pharmaceutically-acceptable carrier and (ii) a compound, or a pharmaceutically acceptable salt thereof, wherein the compound competes for binding to a CatSper1 channel with a CatSper1 modulator represented by the formula:

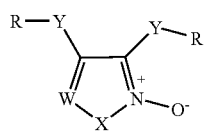

wherein W is CR' or N; R' is a lower alkyl or a hydrogen; X is O or S; Y, independently for each occurrence, is C=O, C=S, or $SO_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl. In one embodiment, W is N. In another embodiment, X is O. In another embodiment, Y is C=O. In another embodiment, R' is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl.

In some embodiments, the compositions of the invention further comprise at least one additional contraceptive agent. In some embodiments, the additional contraceptive agent is an oral contraceptive, for example, a hormonally-based oral contraceptive. In some embodiments, the composition comprises a combination of additional oral contraceptives, such as an estrogen and a progestin. In one embodiment, the additional contraceptive agent is selected from norgestimate (NGM), ethinyl estradiol (EE), 17-β estradiol (E2), norethindrone, norethindrone acetate, chlormadione acetate, norethynodrel, norgestrel, medroxyprogesterone acetate, megeskol acetate, lynestrenol, quingeskone, gestodine, desogestrel, ethynodiol acetate, and dimethisterone. In some embodiments, the compositions of the invention further comprise at least one anti-erectile dysfunction agent. In one embodiment, the anti-erectile dysfunction agent is selected from a vascular smooth muscle relaxant, an α-adrenoceptor antagonist, and a male hormone. In some embodiments, the compositions of the invention are formulated as an injection, a transdermal patch, a bioerodable implant, a lubricant, a moisturizer, a foam, a jelly, or a sponge.

The invention provides pharmaceutically acceptable preparations comprising the compounds described above formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Methods of preparing these formulations or compositions include the step of bringing into association one or more agents of the present invention with the carrier and, optionally, one or more accessory ingredients. In general, the formulations are prepared by uniformly and intimately bringing into association one or more agents of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A agent of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more agents of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of one or more agents of this invention include powders, sprays, ointments, pastes, creams, lotions, gels, solutions, patches and inhalants. The active agents may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent of the present invention to the body. Such dosage forms can be made by dissolving or dispersing the subject compound in the proper medium. Absorption enhancers can also be used to increase the flux of the subject agent across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

In one embodiment, the compounds of the invention are formulated into oral compositions and mixed into a kit with other oral compositions that lack the active compounds of the invention. Such kits may have "active" compositions and "placebo" compositions. Each kit may contain enough dosage units for administration of one regimen cycle for at least 18 to 35 days. In an illustrative embodiment, a kit may include sufficient dosage units for one menstrual cycle, such as one table daily, where some of the tablets contain the compound as an active ingredients and other tablets are placebos. The tablets containing the compound may be administered for a part of the menstrual cycle where sexual activity, ovulation and/or fertility is expected to peak, and the placebo pills are administered at other times. Such dosage regimens have the advantage of reducing the cumulative amount of exposure to the compounds—and thereby minimize any undesirable effects—while facilitating compliance with a daily dosing regimen. Such dosing regimens are not limited to compositions administered to females. For compositions intended for male administration, the timing of the dosages may likewise be synchronized to the female's menstrual cycle. In some embodiments, the placebo compositions, while lacking the active CatSper inhibiting compounds or lacking the hypermotility inhibiting compounds of the invention, may contain other hormones or contraceptives or active ingredients which do not modulate CatSper activity or hypermotility.

In some embodiments, the compounds of the invention are formulated into implantable devices, such as devices for the subcutaneous delivery of drugs. For example, Norplant® systems which use a silicone elastomer may be adapted for the delivery of the compounds of the invention to, for example, women (See U.S. Pat. Nos. 4,957,119, and 5,088,505 as well as Haukkamaa et al. (1992) Contraception 45, 1, pgs. 49-55). Similarly, U.S. Pat. No. 5,733,565 describes implantable devices that may be used to administer the compounds of the invention to, for example, men. In addition, the compounds of the invention may be administered in conjuction with contraceptive devices. These include, for example, condoms, and penile caps (see U.S. Pat. No. 5,458,114) for men, and sponges, diaphragms, spermicidal gels and foams, and female condoms for women. The compounds may also be administered in conjunction with a lubricant.

One aspect of the invention provides contraceptive or birth control devices, such as condoms. One aspect of the invention provides condoms comprising the compounds of the invention. In one embodiment, the contraceptive devices comprise a condom and a composition comprising a CatSper inhibitor or an inhibitor of sperm hypermotility. Such a device may be suitable for the end user to apply the compound to the condom prior to use. Types of condoms that may be used include those described in U.S. Patent Publication Nos. 2006-0048784, 2004-0118408, 2005-0076916 and 2004-01636529.

In one embodiment, the contraceptive device comprises (i) a condom; and (ii) a compound represented by the structural formula represented by the formula

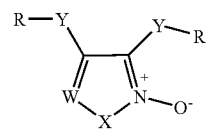

wherein W is CR' or N, wherein R' is a lower alkyl or a hydrogen; X is O or S; Y, independently for each occurrence, is C=O, C=S, or SO2; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl, or with a pharmaceutically acceptable salt of said compound. In one embodiment, W is N. In another embodiment, X is O. In another embodiment, Y is C=O. In another embodiment, R' is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl. In another embodiment, the compound is represented by any one of structural formulas (II)-(VI).

In one embodiment, the condom comprises one or more of a lubricant, a warming composition, a spermicidal agent, a desensitizer or a erectogenic composition. Desensitizer lubricants are described in U.S. Patent Publication No. 2002010344. Spermicidal agents include Nonoxonyl-9 and derivatives (see U.S. Patent Publication No. 20010036965). U.S. Patent Publication No. 2005-0042249 describes warming agents. Condoms with an erectogenic compositions are described in U.S. Patent Publication No. 20020103414. Erectogenic compositions include those comprising a vasodilator, including nitrates, long and short acting alpha-adrenoceptor blockers, ergot alkaloids, anti-hypertensives and the prostaglandins.

The compositions of the inventions may also be used as control agents for in vitro assays employing spermatozoa. For example, the compounds of the invention may be used as a positive controls to show that spermatozoa are competent to downregulate their hyperactivity behavior. This may be useful when a test compound suspected of being able to downregulate CatSper1 activity fails to inhibit sperm hypermotility in an in vitro assay, and it is necessary to determine whether this failure is attributed to the properties of the test compound or to experimental conditions that prevent any type of hyperactivity inhibition.

IV. Modulating CatSper1/Spermatozoa Function

The invention further provides methods of decreasing the activity of a CatSper channel, for example a CatSper1 channel. In one embodiment, the CatSper1 channel is in a cell, such as in a spermatozoon. In some embodiments, the method of decreasing CatSper1 channel activity comprises contacting a cell that expresses CatSper1, such as a spermatozoon, with a compound, or a salt thereof, represented by the formula:

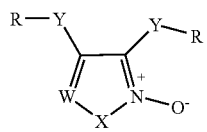

wherein W is CR' or N; R' is a lower alkyl or a hydrogen; X is O or S; Y, independently for each occurrence, is C=O, C=S, or SO₂; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl. In one embodiment, W is N. In another embodiment, X is O. In another embodiment, Y is C=O. In another embodiment, R' is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl. In certain embodiments, the compound is represented by any one of formulas (II-VI).

In some embodiments, the cell expressing the CatSper1 channel is in a mammal, such as in a human. In one embodiment, the mammal is a non-human mammal. The mammal may be a female or a male. Compositions suitable for administering the compounds to the mammals are described above.

The invention also provides methods of decreasing $Ca^{+2}$ influx into a cell. In preferred embodiments, the cell is a spermatozoon. In some embodiments, the method of decreasing $Ca^{+2}$ influx into a cell comprises contacting the cell, such as a spermatozoon, with a compound, or a salt thereof, represented by the formula:

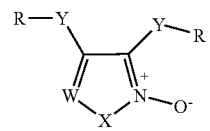

wherein W is CR' or N; R' is a lower alkyl or a hydrogen; X is O or S; Y, independently for each occurrence, is C=O, C=S, or SO₂; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl. In one embodiment, W is N. In another embodiment, X is O. In another embodiment, Y is C=O. In another embodiment, R' is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl. In certain embodiments, the compound is represented by any one of formulas (II-VI).

The invention also provides methods of selectively decreasing the hyperactivity of a spermatozoon. In some embodiments, the hyperactivity of the spermatozoon is decreased by at least 20, 30, 40, 50, 60, 70, 80, 90, 95, 96, 97, 98 or 99%. In some embodiments, the hyperactivity of the spermatozoon is decreased without inhibiting the motility of the sperm, or without substantially inhibiting the motility of the sperm. By not substantially inhibiting the motility of the sperm it is meant that the motility of the sperm is not reduced by more than about 15, 20 or 25%. In some embodiments, the hyperactivity of the spermatozoon is decreased without inhibiting its viability, or without substantially inhibiting viability of the sperm. By not substantially inhibiting the viability of the sperm it is meant that the viability of the sperm is not reduced by more than 15, 20 or 25%. In some embodiments, the hyperactivation of the spermatozoon is inhibited ex vivo, such as in Example 2 of the exemplification. In other embodiments, the hyperactivation of the spermatozoon is inhibited in vivo, such as in a female inseminated with spermatozoa.

In some embodiments, the method of decreasing the hyperactivity of a spermatozoon comprises contacting the spermatozoon with a compound, or a salt thereof, represented by the formula:

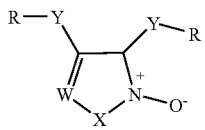

wherein W is CR' or N; R' is a lower alkyl or a hydrogen; X is O or S; Y, independently for each occurrence, is C=O, C=S, or SO$_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl. In one embodiment, W is N. In another embodiment, X is O. In another embodiment, Y is C=O. In another embodiment, R' is H. In another embodiment, the two Y—R substituents are identical. In some embodiments, the R represents, independently for each occurrence, a substituted or unsubstituted branched alkyl (such as isopropyl or t-butyl), branched alkenyl, branched alkynyl, aryl, heteroaryl, carbocyclyl, heterocyclyl, aralkyl, heteroaralkyl, carbocyclylalkyl, or heterocyclylalkyl. In certain embodiments, R represents, independently for each occurrence, a substituted or unsubstituted aryl or heteroaryl. In certain embodiments, the compound is represented by any one of formulas (II-VI).

V. Decreasing Fertility in Males or Females

Another aspect of the invention provides methods of decreasing fertility. These methods are based, in part, on the administration of the novel classes of compounds provided by the invention. These compounds may be administered to a male such that the compounds contact the sperm while it is still in the male. The compounds may also be administered to a male birth control device, such as a condom or penile cap, such that the sperm contacts the compounds shortly after ejaculation. The compounds may also be administered to a female, such that the sperm contact the compounds once they enter the female. When the compound is administered to a female, the compound might be administered systemically, such as orally, intradermally or by injection, or may be administered locally, such as to the vagina, uterus or fallopian tubes. The compounds may also be administered as part of female birth control devices, such as diaphragms or sponges. When administered orally, the compounds may be coadministered with other oral contraceptives, whether as one composition comprising the compound and the contraceptive or as two compositions, each containing an active compound.

The invention provides methods of decreasing the fertility of a male subject by administering a compound to the subject which decreases CatSper channel activity, for example CatSper1 channel activity; which preferentially inhibits sperm hyperactivity over sperm motility; or both. In another aspect, the invention provides a method of causing reversible infertility in a male subject by administering a compound to the subject which decreases CatSper channel activity, e.g. CatSper1 channel activity; which preferentially inhibits sperm hyperactivity over sperm motility; or both. In another aspect, the invention provides a method of contraception in which a compound which decreases CatSper1 channel activity, which preferentially inhibits sperm hyperactivity over sperm motility, or both, is administered to a male or female subject. In each of the foregoing embodiments, the compound can be formulated in an injection, a transdermal patch, a bioerodable implant, a lubricant, a moisturizer, a foam, a jelly, or a sponge. If the subject is a female, the compound can be administered into at least one of the vagina, uterus or fallopian tubes.

Because most antagonists of CatSper1 channel expression or activity will be reversible or will affect only mature sperm, the effects of such compounds on fertility will be reversible because the molecules will be cleared from the body over time and new sperm are constantly being produced. Thus, antagonists of CatSper1 channel expression or activity can be used as human contraceptives because they can cause reversible infertility. Such contraceptives can be taken orally or parenterally (e.g., injection, transdermal patch, or bioerodable implant) by females if they achieve sufficient concentrations in the vagina, uterus or fallopian tubes to effectively inhibit CatSper1 channel activity and thereby decrease sperm hyperactivation and the ability of sperm to penetrate the zona pellucida (ZP). Similarly, such contraceptives can be taken orally or parenterally by males if they achieve sufficient concentration in the testes or seminal fluids to effectively inhibit CatSper1 channel expression or activity, and thereby decrease sperm hyperactivation and the ability of sperm to penetrate the ZP. Alternatively, such compounds can be formulated into lubricants, moisturizers, foams or jellies for use with prophylactics, cervical caps, or contraceptive vaginal sponges, foams or jellies.

In another series of embodiments, the compounds described herein can be used as contraceptives to treat non-human mammals. These embodiments are similar to those described above for human contraception. Such contraceptives can be used with respect to domesticated animals that are maintained as pets, with respect to other commercially valuable domesticated animals (e.g., cows, sheep, horses), or with respect to animal nuisances (e.g., mice, rats, raccoons, gophers). In some embodiments, the contraceptives are orally available and can be mixed into food sources for the animals. In other embodiments, the contraceptives can be administered parenterally (e.g., injection, transdermal patch, or bioerodable implant).

In some embodiments, the compounds used to reduce fertility or to cause temporary infertility are represented by the following structure:

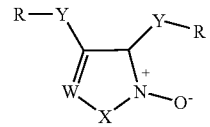

wherein W is CR' or N, wherein R' is a lower alkyl or a hydrogen; X is O or S; Y, independently for each occurrence, is C=O, C=S, or SO$_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl, or a pharmaceutically acceptable salt thereof. In another embodiment, the compound is represented by any one of structural formulas (II)-(VI).

In other embodiments, the compounds used to reduce fertility or to cause temporary infertility compete with CatSper1 channel-binding agents represented by the following structure:

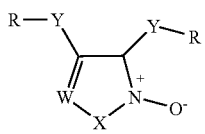

wherein W is CR' or N, wherein R' is a lower alkyl or a hydrogen; X is O or S; Y, independently for each occurrence, is C=O, C=S, or $SO_2$; and R, independently for each occurrence, represents a substituted or unsubstituted alkyl, alkenyl, alkynyl, aryl, heteroaryl, carbocyclyl, heterocyclyl, aralkyl, heteroaralkyl, carbocyclylalkyl, or heterocyclylalkyl, or a pharmaceutically acceptable salt thereof. In another embodiment, the compound is represented by any one of structural formulas (II)-(VI).

In other embodiments, the compounds used to reduce fertility or to cause temporary infertility are coadmistered with other contraceptive agents. In some embodiments, the additional contraceptive agents are administered to the same subject, male or female, to which the compound is adminstered. In other embodiments, the additional contraceptive agents are administered to the sexual partner of the recipient of the compound, such that at least one of the sperm donor and sperm recipient receives the additional contraceptive treatment.

The invention also provides contraceptive methods where a compound is administered to both sexual partners, i.e. to both the sperm donor and the sperm recipient. In some embodiments, the compound (i) is represented by any one of formulas (I-VI), or (ii) competes for binding to a CatSper1 channel with a compound represented by any one of formulas (I-VI).

The invention further provides agents for the manufacture of medicaments to reduce fertility in a male, in a female, or in both. Any methods disclosed herein for reducing fertility by administering a compound to an subject may be applied to the use of the compound in the manufacture of a medicament to reduce fertility in the subject.

VI. Business Methods

In another aspect, the present invention provides a method of conducting a drug discovery business comprising: identifying, by the assays of the invention, one or more compounds which antagonize CatSper activity and/or inhibit sperm hyperactivation; determining if an compound identified in such an assay, or an analog of such an compound, inhibits sperm hyperactivation; conducting therapeutic profiling of a compound identified as an antagonist for efficacy and toxicity in one or more animal models; and formulating a pharmaceutical preparation including one or more antagonist compounds identified as having an acceptable therapeutic profile.

In one embodiment, the compound antagonizes a CatSper Channel activity. In another embodiment, the compound antagonizes a CatSper1 Channel activity. In another embodiment, the compound inhibits sperm hyperactivation.

In one embodiment, the drug discovery business further includes the step of establishing a system for distributing the pharmaceutical preparation for sale, and may optionally include establishing a sales group for marketing the pharmaceutical preparation.

In yet another aspect, the present invention provides a method of conducting a contraceptive medicine business comprising: providing a pharmaceutical preparation discovered through the methods of a drug discovery business, wherein said preparation inhibits the activity of a CatSper Channel and/or inhibits sperm hyperactivation; providing instructions to physicians, health care providers, and/or patients (e.g., users) for the administration of an amount of said pharmaceutical preparation effective to inhibit the activity of a CatSper Channel, wherein said effective amount is sufficient to prevent pregnancy.

In one embodiment, the method further includes the step of establishing a system for distributing the pharmaceutical preparation for sale, and may optionally include establishing a sales group for marketing the pharmaceutical preparation.

In one embodiment, the preparation is for administration to female patients. In another embodiment, the preparation is for administration to male patients. In still another embodiment, the preparation is formulated as a lubricant or cream for use with a contraceptive device including, but not limited to, a condom, diaphragm, sponge, or other barrier birth control device.

In any of the foregoing, the compound that inhibits CatSper Channel activity may be identified or characterized using one or more of (i) the bacterial expression assay described herein or (ii) the sperm motility/hyperactivation assay described herein.

In any of the foregoing, the compound may be further tested for (i) efficacy, (ii) safety, (iii) side-effects, (iv) specificity (e.g., preferential activity) for sperm hyperactivation over sperm death, (v) specificity (e.g., preferential activity) for sperm hyperactivation over sperm motility, (vi) specificity (e.g., preferential activity) for antagonizing CatSper Channel activity over the activity of a voltage gating calcium channel, (vi) specificity (e.g., preferential activity) for antagonizing CatSper Channel activity over HERG activity or (vii) specificity (e.g., preferential activity) for different heteromeric forms of CatSper channels.

In certain embodiments of any of the foregoing, the initially identified CatSper Channel antagonist and/or compound that inhibit sperm hyperactivation can be subjected to further lead optimization, e.g., to further refine the structure of a lead compound so that potency and activity are maintained but balanced with important pharmacological characteristics including: solubility, permeability, bioavailability, toxicity, mutagenicity, pharmacokinetics—absorption, distribution, metabolism, elimination of the drug Structural modifications are made to a lead compound to address issues with the parameters listed above. These modifications however, must take into account possible effects on the molecule's potency and activity. For example, if the solubility of a lead compound is poor, changes can be made to the molecule in an effort to improve solubility; these modifications, however, may negatively affect the molecule's potency and activity. SAR data are then used to determine the effect of the change upon potency and activity. Using an iterative process of structural modifications and SAR data, a balance is created between these pharmacological parameters and the potency and activity of the compound.

Candidate antagonists, or combinations thereof, must them be tested for efficacy and toxicity in animal models. Such therapeutic profiling is commonly employed in the pharmaceutical arts. Before testing an experimental drug in humans, extensive therapeutic profiling (e.g., preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

Briefly, one of skill in the art will recognize that the identification of a candidate compound which antagonizes CatSper Channel activity and/or inhibits sperm hyperactivation in a drug based screen is a first step in developing a pharmaceutical preparation useful as a contraceptive agent. Administration of an amount of said pharmaceutical preparation effective to successfully prevent pregnancy (i.e., to act as a useful contraceptive agent) must be both safe and effective. Early stage drug trials, routinely used in the art, help to address concerns of the safety and efficacy of a potential pharmaceutical. In the specific case of the subject antagonists, efficacy of the pharmaceutical preparation could be readily evaluated in a mouse or rat model. Briefly, male mice could be administered varying doses of said pharmaceutical preparations over various time schedules. Control male mice can be administered a placebo (e.g., carrier or excipient alone). The male mice are then allowed to mate freely by placing said male into cages with female mice, and measuring rate of conception over time. Given the efficacy of currently available forms of birth control, an effective contraception should be at least 80% effective, preferably 85% effective, more preferably 90% effective, most preferably 95%, 96%, 97%, 98%, 99% or greater than 99% effective in preventing pregnancy.

In one embodiment, the step of therapeutic profiling includes toxicity testing of compounds in cell cultures and in animals; analysis of pharmacokinetics and metabolism of the candidate drug; and determination of efficacy in animal models of diseases. In certain instances, the method can include analyzing structure-activity relationship and optimizing lead structures based on efficacy, safety and pharmacokinetic profiles. The goal of such steps is the selection of drug candidates for pre-clinical studies to lead to filing of Investigational New Drug ("IND") applications with the U.S. FDA and/or similar applications with similar regulatory authorities prior to human clinical trials.

Between lead optimization and therapeutic profiling, one goal of the subject method is to develop compound which has minimal side-effects. In the case of antagonists, the lead compounds will have clinically acceptable effects on vasodilatation (i.e., dizziness, hypotension, headache, flushing, edema, etc.), myocardial ischemia, hypotension, bradycardia, transient asystole, exacerbation of heart failure, ventricular dysfunction, SA node or AV conduction disturbances, or plasma digoxin levels.

By "toxicity profiling" is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to mis-regulated cell growth, proliferation, and differentiation. Many forms of cancer are particularly devastating diseases which cause severe pain, loss of function of the effected tissue, and death. Chemotherapeutic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat.

In contrast, however, most currently available forms of birth control do not have significant side-effects. Thus, a pharmaceutical preparation of the subject antagonists should have minimal toxicity and side-effects. Toxicity tests can be conducted in tandem with efficacy tests, and male mice administered effective doses of the pharmaceutical preparation can be monitored for adverse reactions to the preparation. Potential adverse reactions associated with a contraceptive agent may include loss of sex drive and behavioral changes. Blood, urine, and fecal samples taken from treated mice can also be monitored to detect any potential adverse changes in immune, kidney, or liver function. Additionally, given that CatSper channels are cation channel, mice receiving said pharmaceutical preparation should also be monitored for any changes in cardiac function indicative of cross reactivity of the with other cation channels. However, as outlined in detail herein, exemplary compounds of the invention are do not significantly cross react with non-CatSper containing channels such as voltage gated calcium channels or HERG channels.

Agents which antagonize CatSper Channel activity and/or sperm hyperactivation, and which are proven safe and effective in animal studies, can be formulated into a pharmaceutical preparation. Such pharmaceutical preparations can then be marketed, distributed, and sold as contraceptive agents.

VII. Methods of Identifying Inhibitors of Sperm Hyperactivation

One aspect of the invention provides methods of identifying compounds that modulate the hyperactivation of sperm. In one embodiment, the methods allow the identification of compounds that inhibit sperm hyperactivation, while others allow the identification of compounds that promote sperm hyperactivation. Applicants invention of novel screening methods is based, in part, on the two unexpected discoveries. First, a fraction (i.e. less than 5%) of compounds that were found to inhibit CatSper1 activity in a bacterial assay were also effective in inhibiting sperm hyperactivity ex vivo (see FIG. 4). Secondly, some compounds which were found to inhibit CatSper1 activity in bacteria were found to be potent activators, not inhibitors, of sperm hyperactivity. FIG. 2 and Example 1 describes an exemplary embodiment of the methods of identifying modulators of sperm hyperactivity.

One aspect of the invention provides a method of identifying a compound that inhibits sperm hyperactivation, the method comprising (a) identifying a compound that inhibits CatSper channel activity; and (b) determining if the compound identified in step (a) inhibits sperm hyperactivation.

A related aspect of the invention provides a method of identifying a compound that promotes sperm hyperactivation, the method comprising (a) identifying a compound that inhibits CatSper channel activity; and (b) determining if the compound identified in step (a) promotes sperm hyperactivation.

A related aspect of the invention provides a method of identifying a compound that inhibits sperm hyperactivation, the method comprising (a) identifying a compound that activates CatSper channel activity; and (b) determining if the compound identified in step (a) inhibits sperm hyperactivation.

A related aspect of the invention provides a method of identifying a compound that promotes sperm hyperactivation, the method comprising (a) identifying a compound that inhibits CatSper channel activity; and (b) determining if the compound identified in step (a) promotes sperm hyperactivation.

Identifying a compound that inhibits or activates CatSper channel activity may be accomplished using standard methods, for the identification of ion channel inhibitors. In some embodiments, the CatSper channel is expressed in a cell and $Ca^{+2}$ flux into the cell, or flux of another ion permeable through CatSper, is monitored as a readout of CatSper activity. The cell used may naturally express the CatSper channel. Alternatively, the CatSper channel may be a recombinant channel expressed in a cell that normally does not express the CatSper channel. In some embodiments, CatSper1, CatSper2, CatSper3, CatSper4, or combinations thereof, are recombinantly expressed in a cell for identifying compounds that activate/inhibit CatSper channel activity. In one embodiment, the CatSper channel is a CatSper1 homomultimer, a CatSper2 homomultimer, or a CatSper1/CatSper2 heteromultimer.

U.S. Patent Application Nos. 2005/0101767 and 2005/0202539 describe bacteria-based screening methodd that may be used to identify CatSper inhibitors. The 2005/0202539 approach is exemplified in Example 2. Screening methods suitable for high-throughput screening are preferred. Screening methods useful to identify modulators of calcium channels are described in WO01/59446, WO0133219A3 and in U.S. Patent Pub. No. 2004/0038421. Gill et al. (2003) *Assay Drug Dev Technol.* (5):709-17 outlines methods of identifying ion channel modulators using flux assays that may be used to identify modulators of CatSper function. In addition, Xia et al. (2004) *Anal Biochem.;* 327(1): 74-81 describes a cell-based high-throughput assay for identifying modulators of calcium channels.

In one embodiment of the cell-based screening methods described above, a cell, if used in step (a), is not a spermatozoon. In some embodiments, the cell is a diploid cell. In another embodiment of the cell-based screening methods, the CatSper channel is a channel selected from CatSper1, CatSper2, CatSper3, CatSper4. In one embodiment, the CatSper channel is a CatSper1 homomultimer, a CatSper2 homomultimer, or a CatSper1/CatSper2 heteromultimer.

In certain embodiments, the CatSper channel is a heteromultimer of two or more of CatSper1, CatSper2, CatSper3, or CatSper4. The screening methods of the invention are not limited to any particualar type of compound. Nucleic acids, polypeptides, peptides, small molecules, natural or synthetic molecules, purified compounds or semi purified compounds, compound libraries, phage display libraries, and the like, may all be used in the screening methods of the invention.

Determining if the compound identified in step (a) inhibits sperm hyperactivation may be accomplished by contacting a sperm, or a sperm population, with the compound identified in step (a). Modulation of hyperactivation of sperm may be monitored using standard methods. Example 2 exemplifies one preferred method. Mortimer and Mortimer, (1990) "Kinematics of human spermatozoa incubated under capacitating conditions" *Journal of Andrology*, Vol 11, Issue 3 195-203 describes an assay for quantitatively detecting sperm hyperactivation. The extent of sperm hyperactivation may be assayed, for example, by comparing the number of spermatozoa that are hyperactivated compared to those that are not. Suitable controls may be used, such as determining the extent of hyperactivation in a spermatozoa population relative to one that is not contacted with the candidate compound.

EXEMPLIFICATION

The invention now being generally described, it will be more readily understood by reference to the following examples, which are included merely for purposes of illustration of certain aspects and embodiments of the present invention and are not intended to be limiting in any way.

The contents of any patents, patent applications, patent publications, or scientific articles referenced anywhere in this application are herein incorporated by reference in their entirety.

Example 1

Identification of Sperm Motility/Hyperactivity Modulators

The general strategy for identifying compounds which modulate CatSper channel activity and sperm hyperactivation is diagrammed in FIG. 2. Libraries of compounds or candidate compounds are first tested in bacteria expressing a CatSper channel, for example the CatSper1 channel, to identify compounds that modulate CatSper channel activity, preferably those that inhibit channel activity. U.S. Patent Pub. Nos. 2005/0101767 and 2005/0202539 describe exemplary methods for screening compounds using bacteria which express the channel. Agents which modulate channel activity are expected to modulate calcium influx into the bacterium.

Candidate compounds are then tested in an in vivo sperm motility/hyperactivation assay to classify them by two criteria: (i) whether they increase, decrease or have no effect on overall sperm motility; and (ii) whether they increase, decrease or have no effect on sperm hyperactivity. Such dual classification results in nine classes of compounds, depending on whether they have an activating, inhibiting or no effect on each of these two assays. Additional structure-based candidate compounds may be further tested in the sperm hyperactivation assay.

Example 2

Screening CatSper1 Channel Modulators Computer-Assisted Sperm Motility Assay

A library of compounds was screened using the methodology outlined in Example 1. A library of compounds was screened to identify compounds that inhibit calcium influx in *E. coli* expressing the CatSper1 channel, as described in U.S. Patent Pub. No. 2005/0202539. Using this approach, a number of compounds that modulated the activity of the CatSper channel expressed in bacteria were identified.

These compounds were further tested to assess their ability to modulate sperm hyperactivation. Sperm were isolated from freshly obtained human semen by discontinuous gradient centrifugation. The sperm were washed with fertilization media containing 0.5% "plasmanate." Sperm were incubated in the fertilization media containing 0.5% plasmanate for ~3 hours at 37° C. Compounds to be tested were suspended to a concentration of about 10 mM in DMSO and stored frozen at −20° C. Compounds were thawed on the day of the experiment and were used either undiluted or diluted 1:50 in DMSO. One μL of the compounds was pipetted into a 96-well PCR plate (individual well volume ~200 μL). DMSO controls were interspersed with the compounds. Sperm were analyzed and diluted to ~5×10$^6$ motile sperm per mL. Approximately 200 μL sperm was added to each well of the plate (yielding final compound concentrations of 50 and 1 uM). The sperm was incubated with the compound for 5 minutes then a sample was analyzed on the computer-assisted sperm analysis (CASA).

Figure 3:
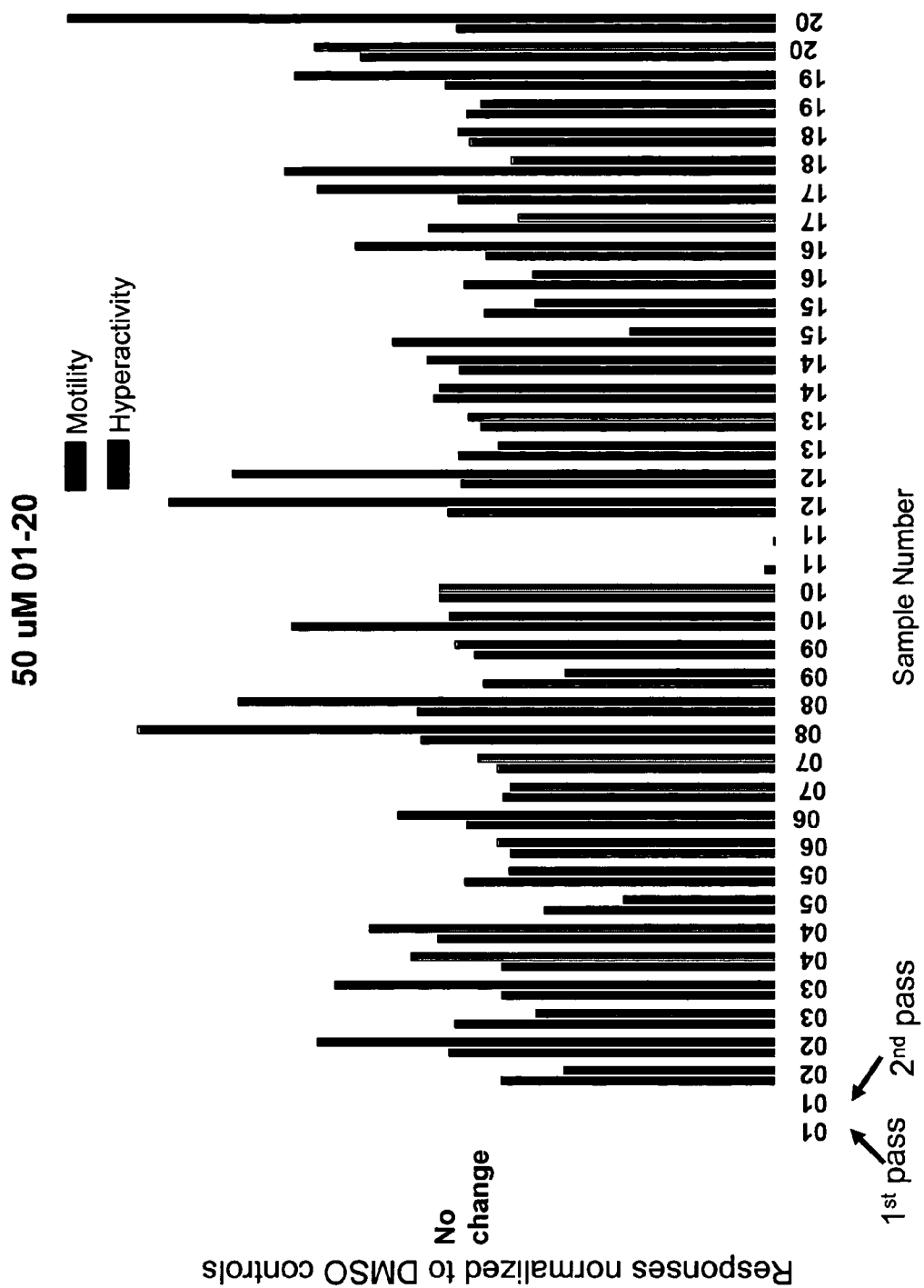
FIG. 3 shows the testing of compounds, in duplicate, for their effects on sperm motility and hyperactivity ex vivo.

The sperm and compound were incubated for 55 minutes more and then re-analyzed. Approximately 6.5 uL of sperm was loaded into a pre-warmed 20 micron deep chamber slide by capillary action. The chamber slide was transferred to the pre-warmed IVOS. Note that IVOS (Hamilton-Thorne) is the particular CASA system used in these experiments. Thirty sequential images of each field were captured by the IVOS over the course of 0.5 seconds, and 20 fields were analyzed from each sample. This yields ~400 individual sperm analyzed per chamber. Sperm count and motion analysis was performed using video microscopy and object recognition/tracking software. FIG. 3 shows data for the screening of multiple compounds in the sperm tracking assay. Compound No. 8 enhances hyperactivity while showing little enhancement on motility; sample No. 15 reduces hyperactivity while showing little inhibition on motility. Screening results for 89 compounds is summarized on FIG. 4.

Example 3

Compound 738 Profoundly and Specifically Inhibits Hyperactivation

Figure 5:
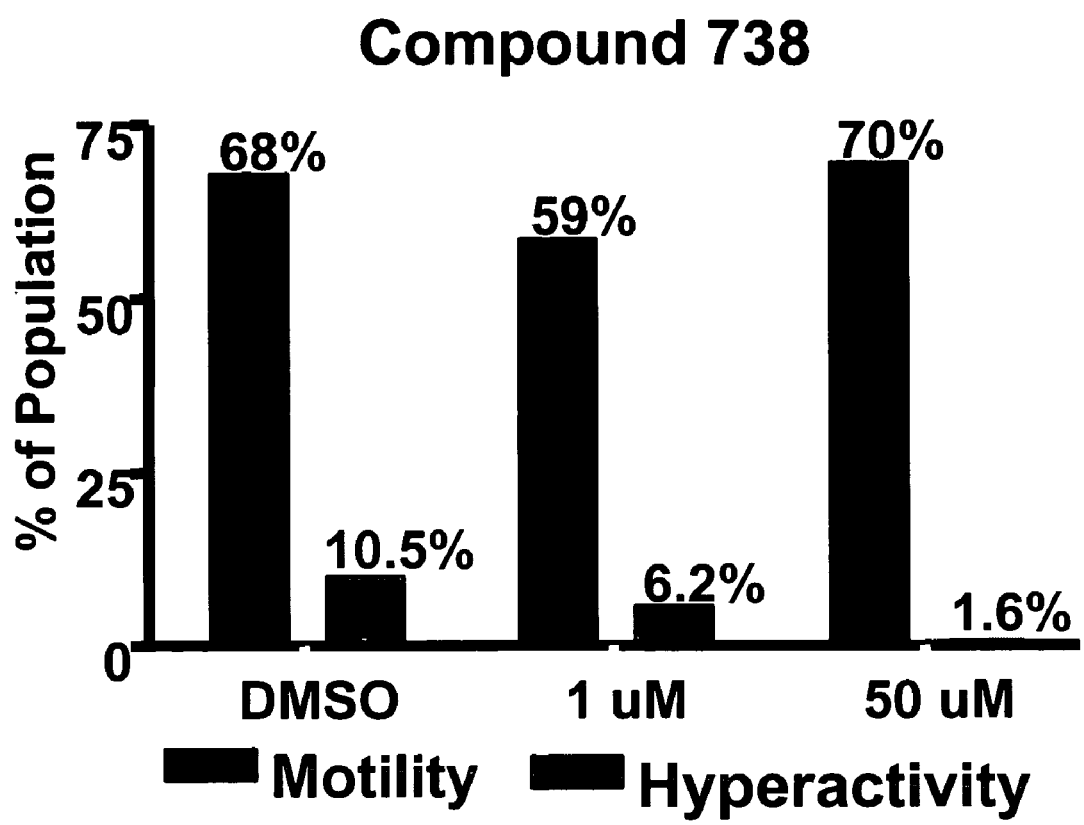
FIG. 5 show the selective inhibition of sperm hyperactivity with compound 738. It shows the concentration dependent inhibition of sperm hyperactivation with compound 738.
Figure 6:
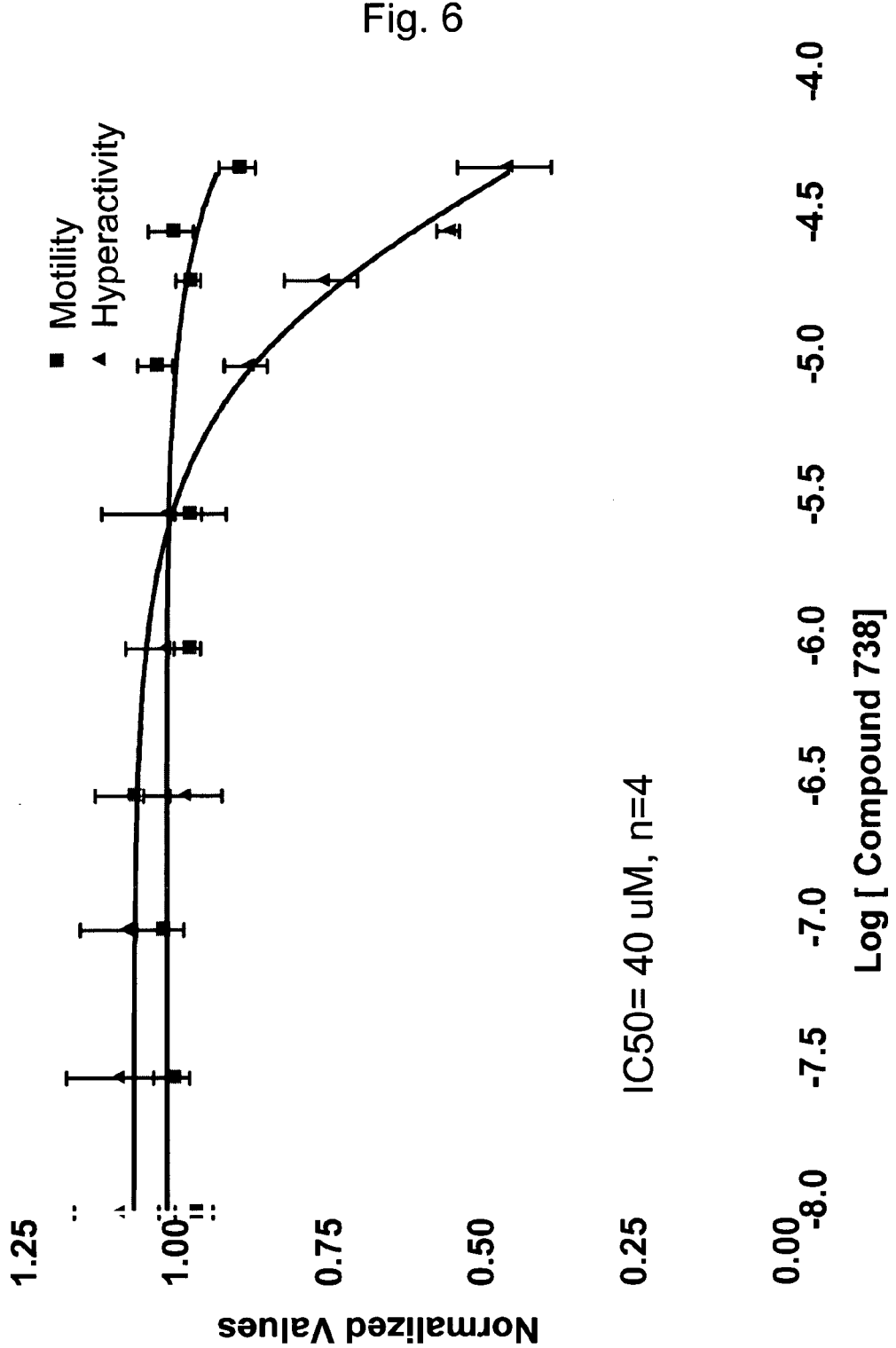
FIG. 6 shows a dose response of sperm hyperactivity in response to compound 738
Figure 8:
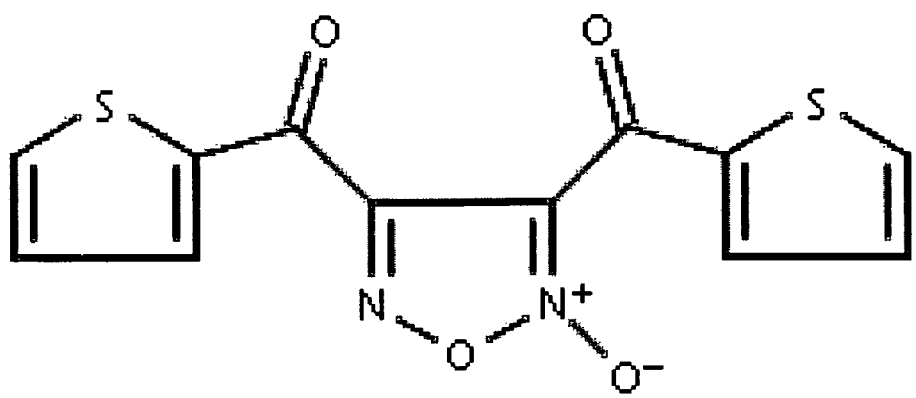
FIG. 8 shows the structures of compounds 738 (top panel) and 354 (bottom panel).
Figure 8:
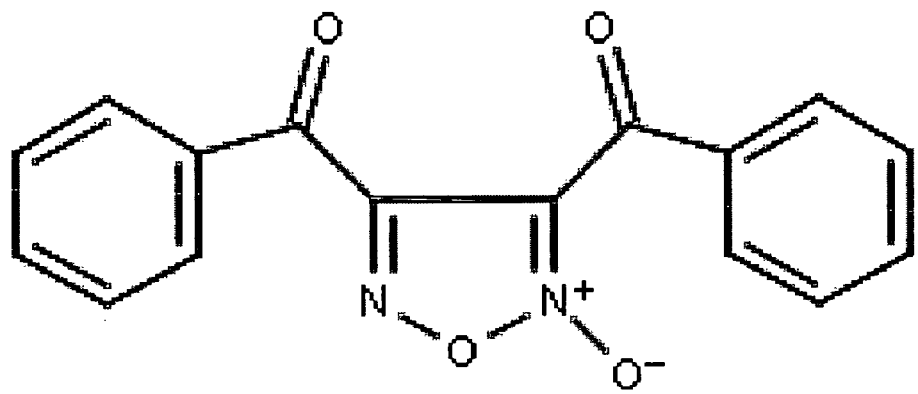
Figure 9A:
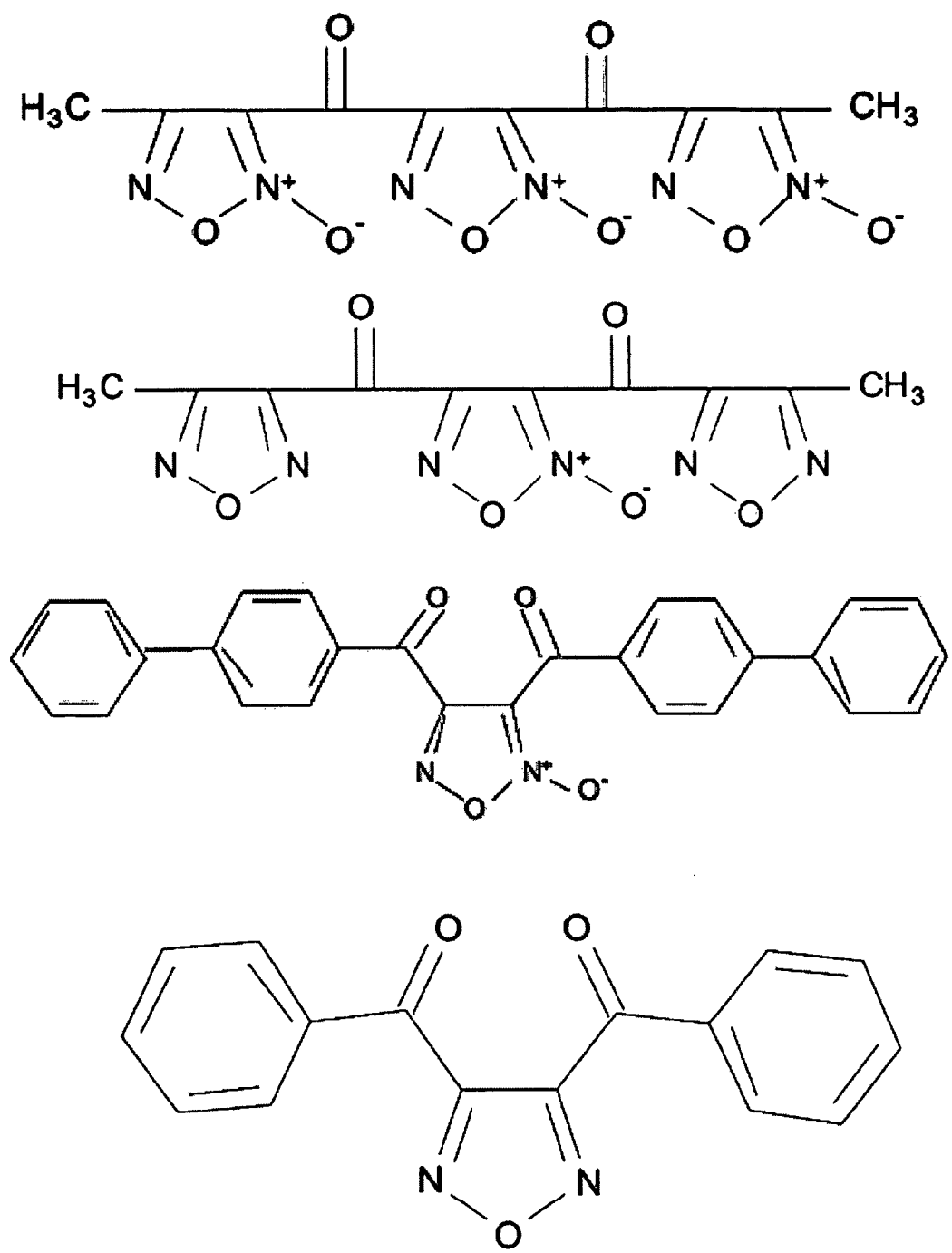
FIGS. 9A-9J show the structures of additional compounds that were tested for specific inhibition of sperm hyperactivation.
Figure 9B:
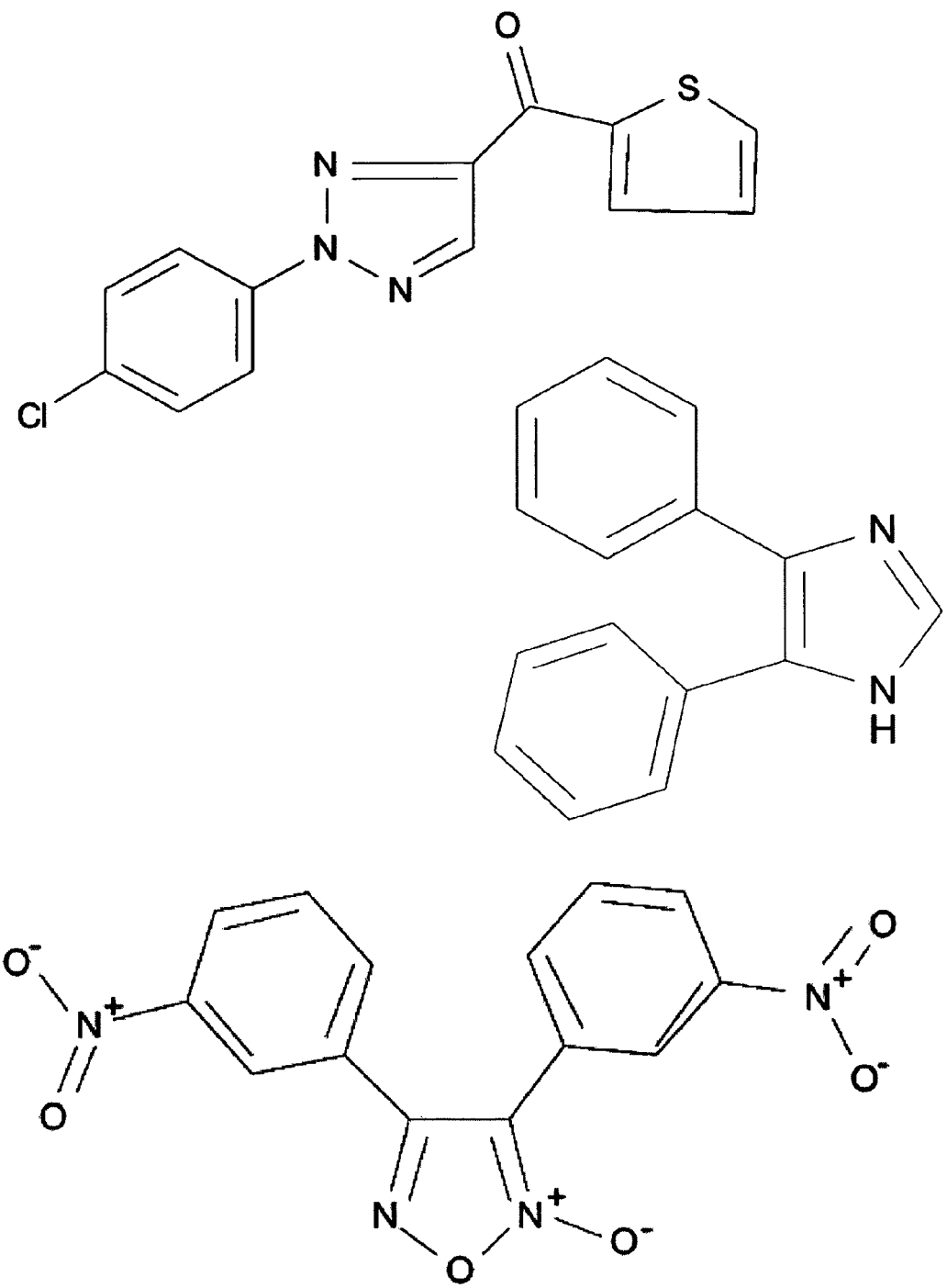
Figure 9C:
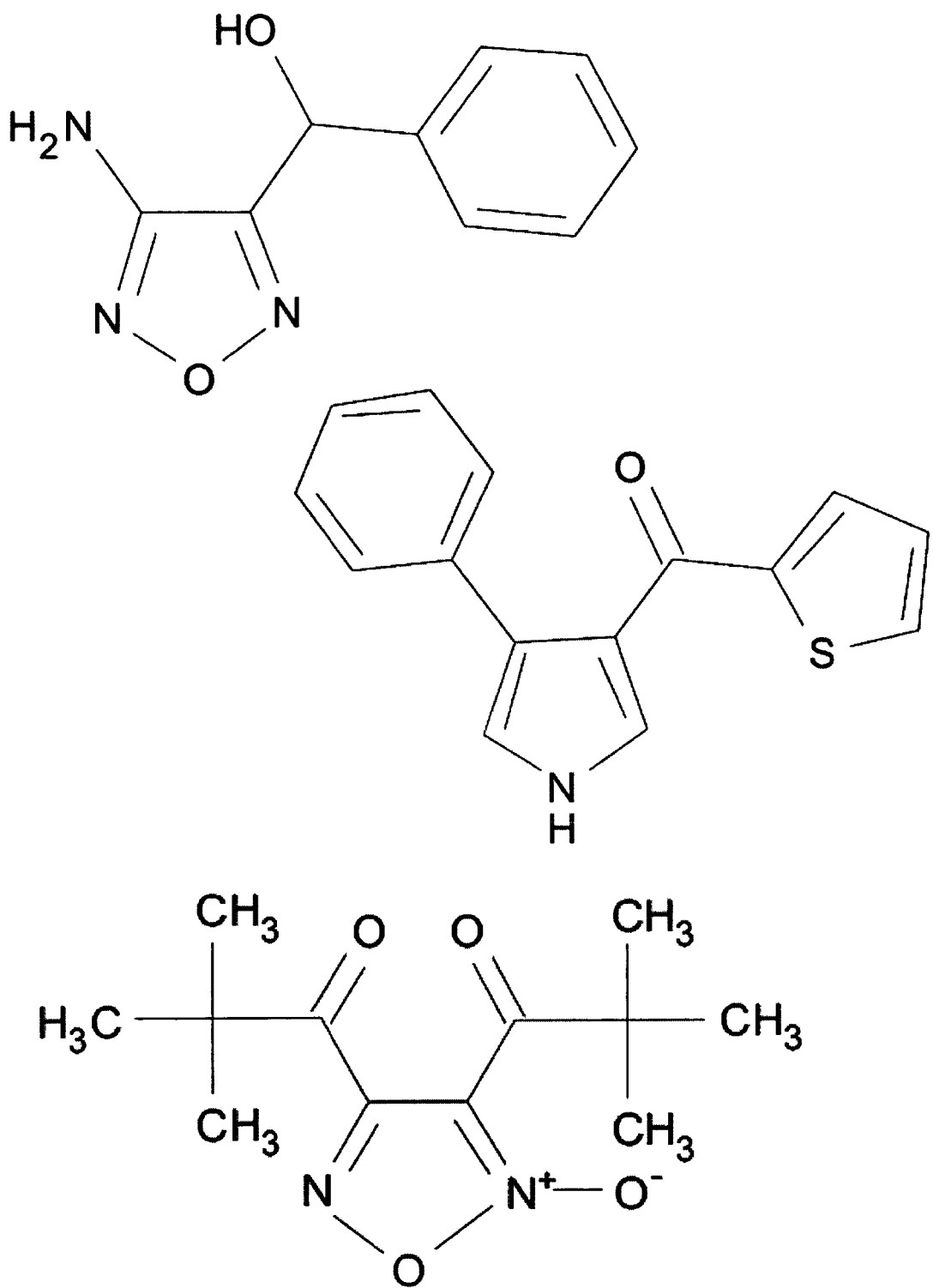
Figure 9D:
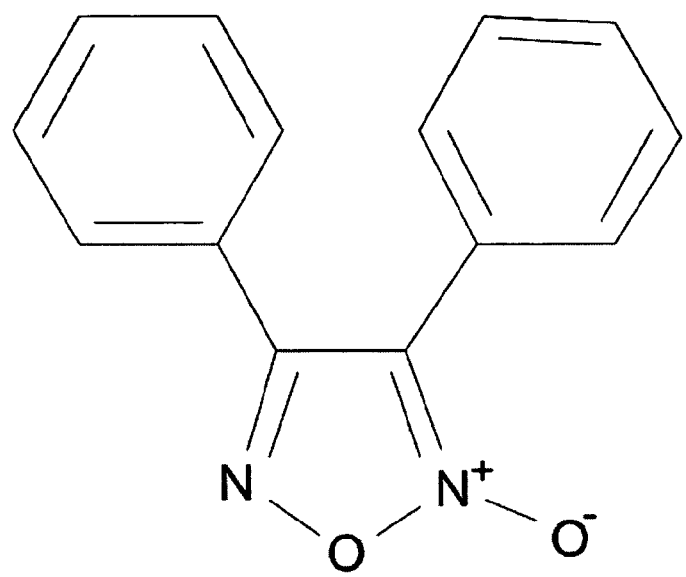
Figure 9D:
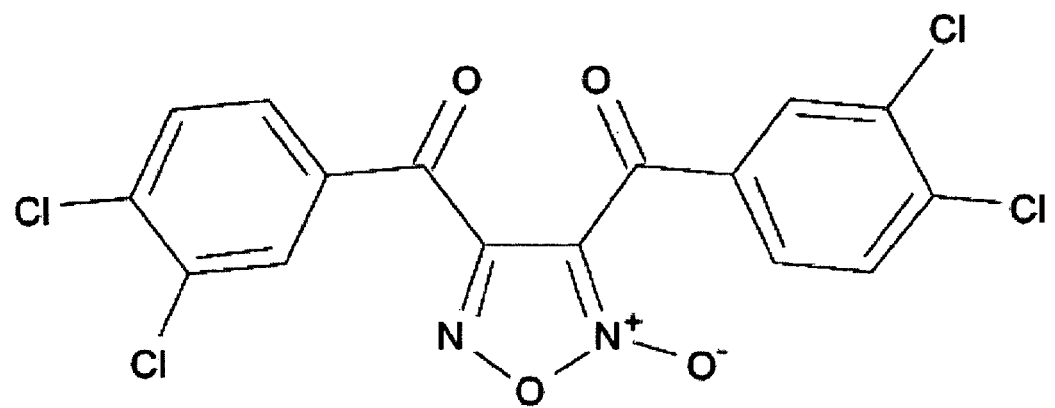
Figure 9E:
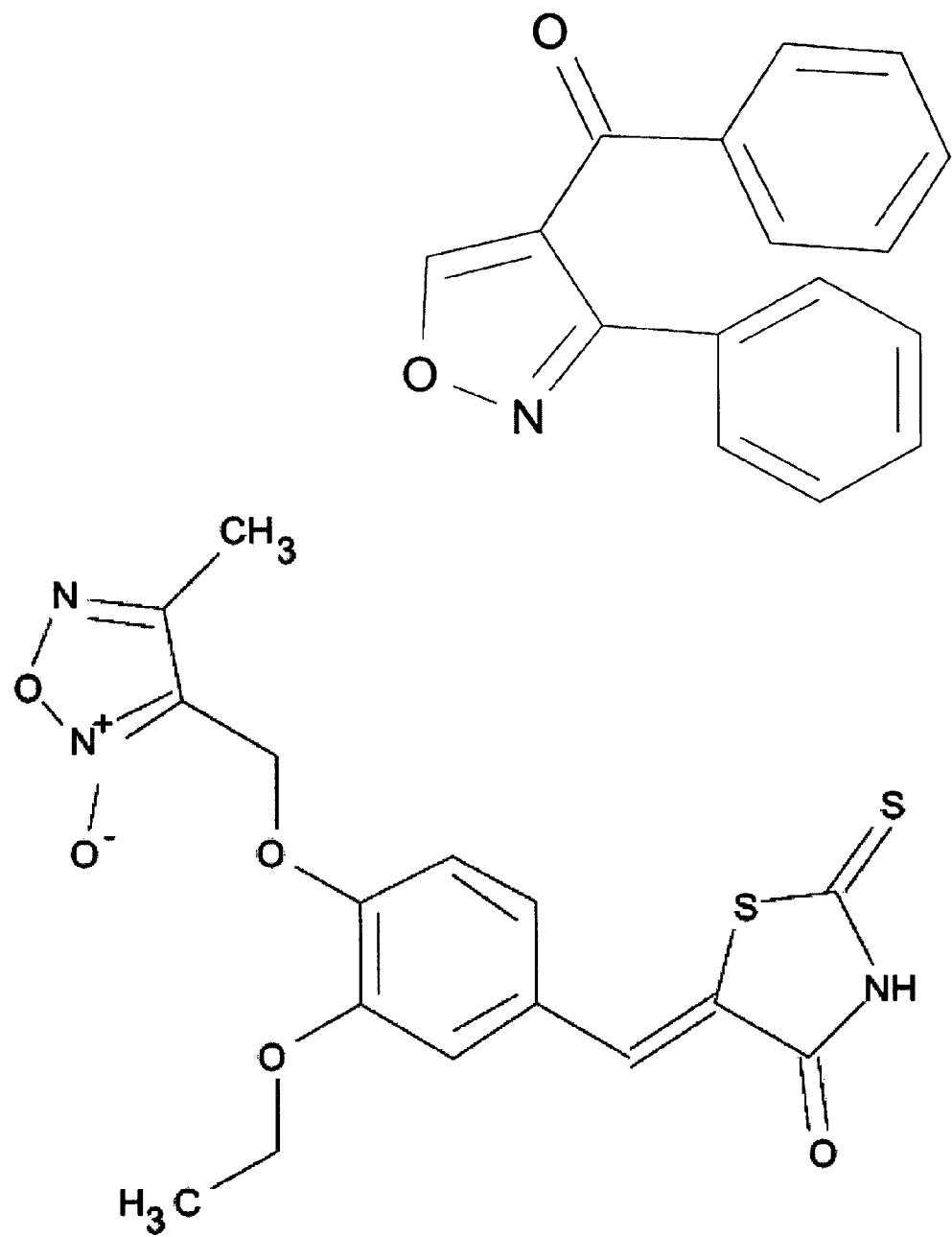
Figure 9F:
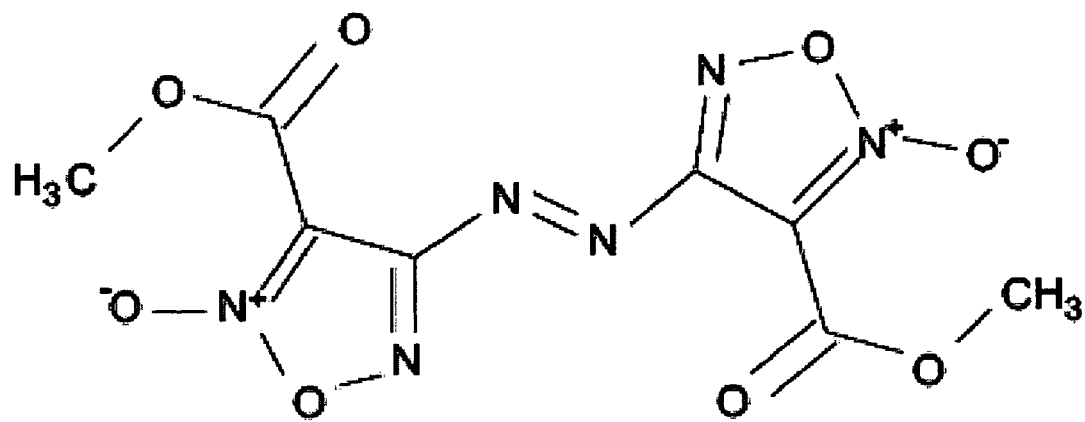
Figure 9F:
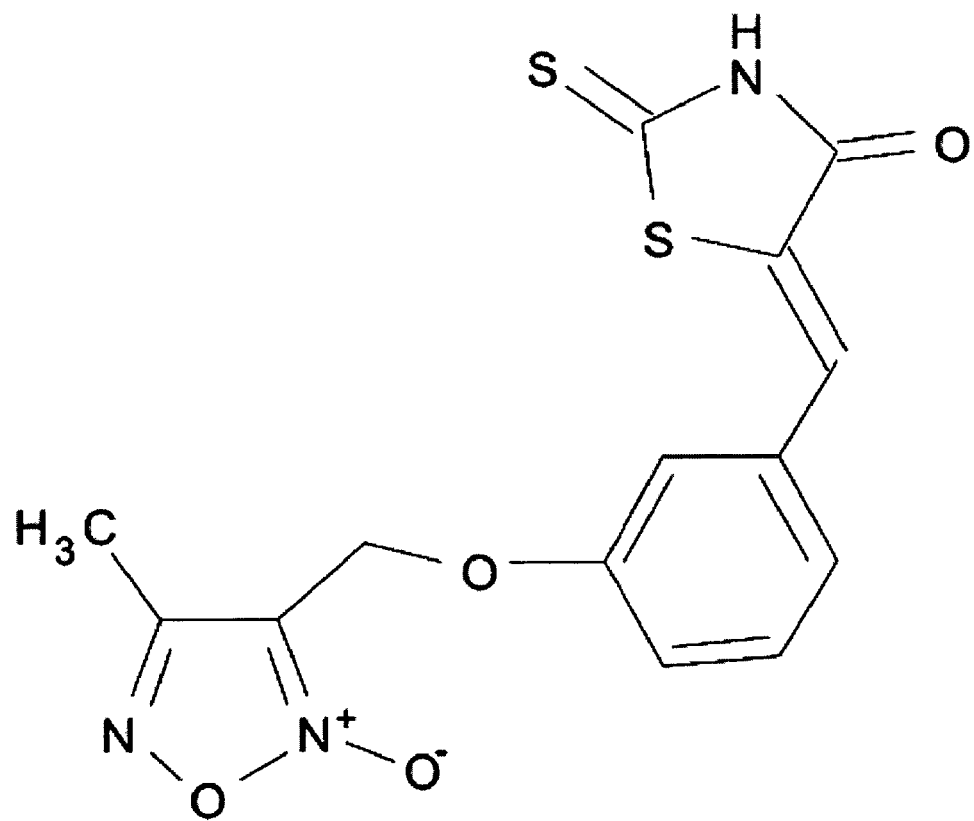
Figure 9G:
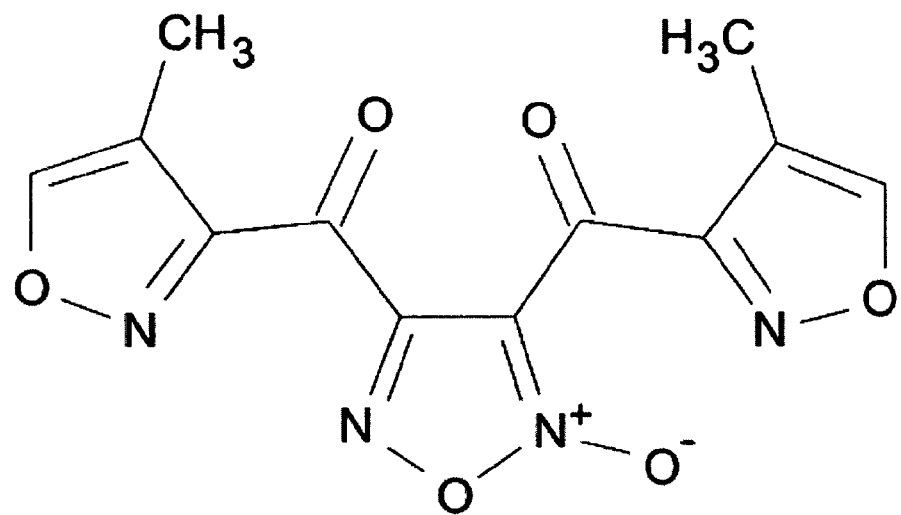
Figure 9G:
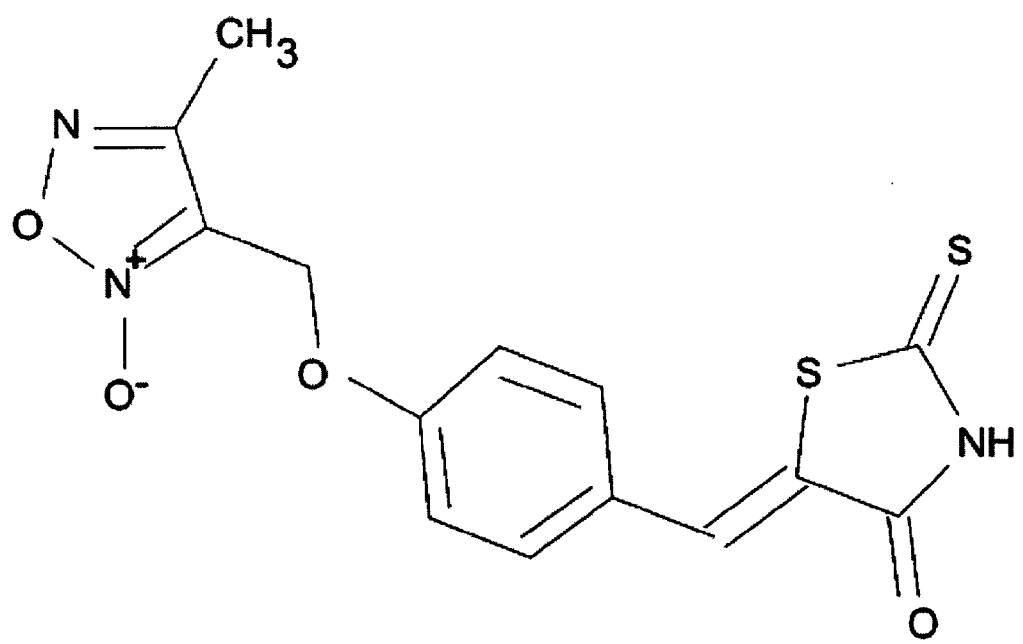
Figure 9H:
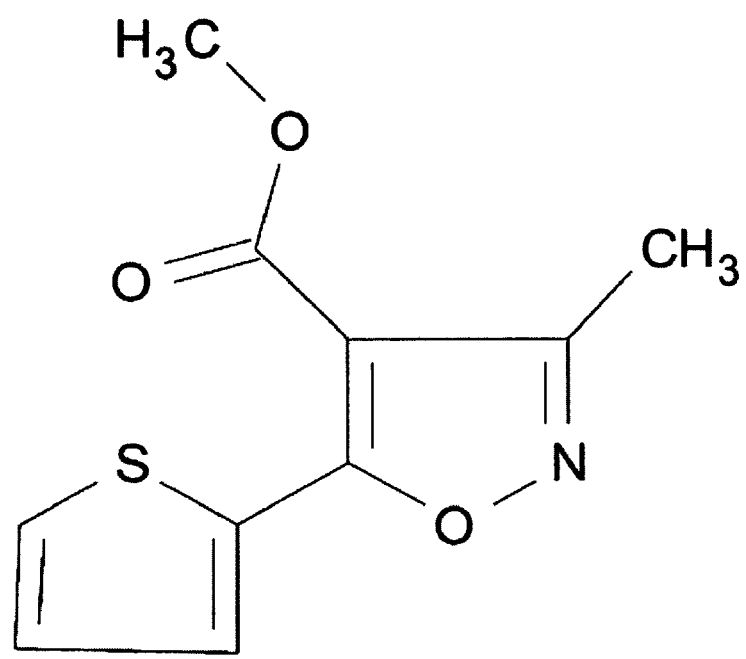
Figure 9H:
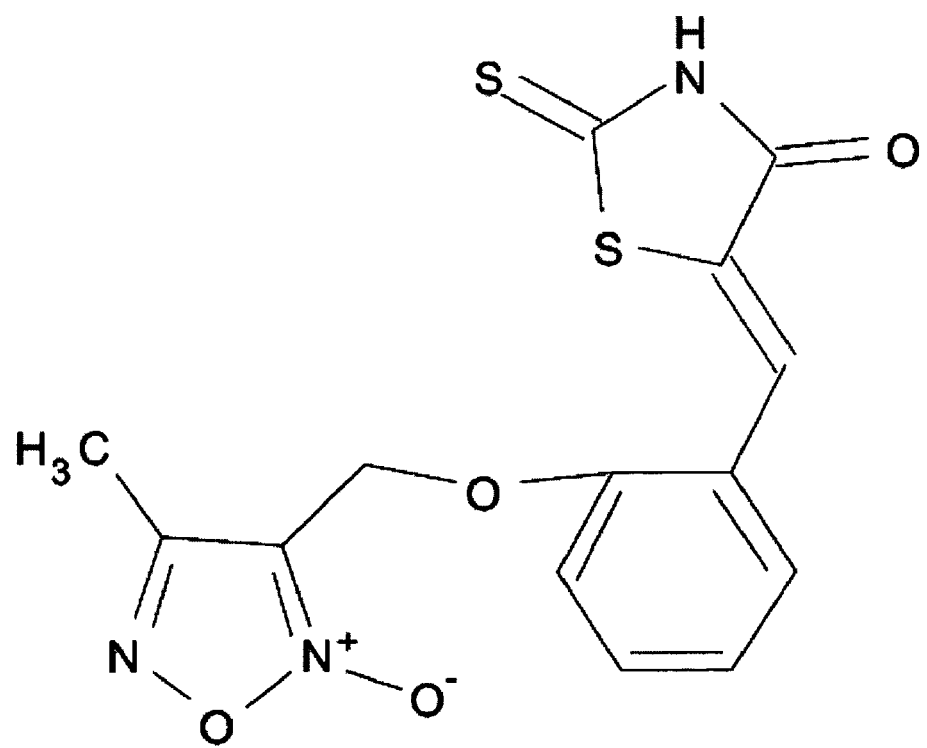
Figure 9I:
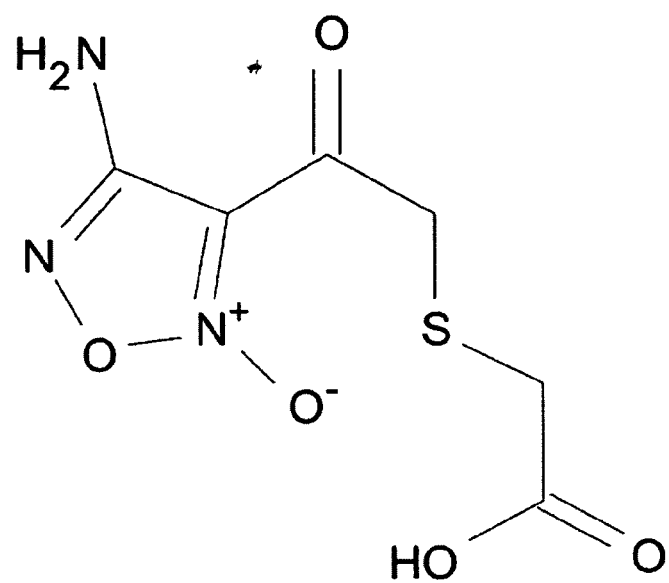
Figure 9I:
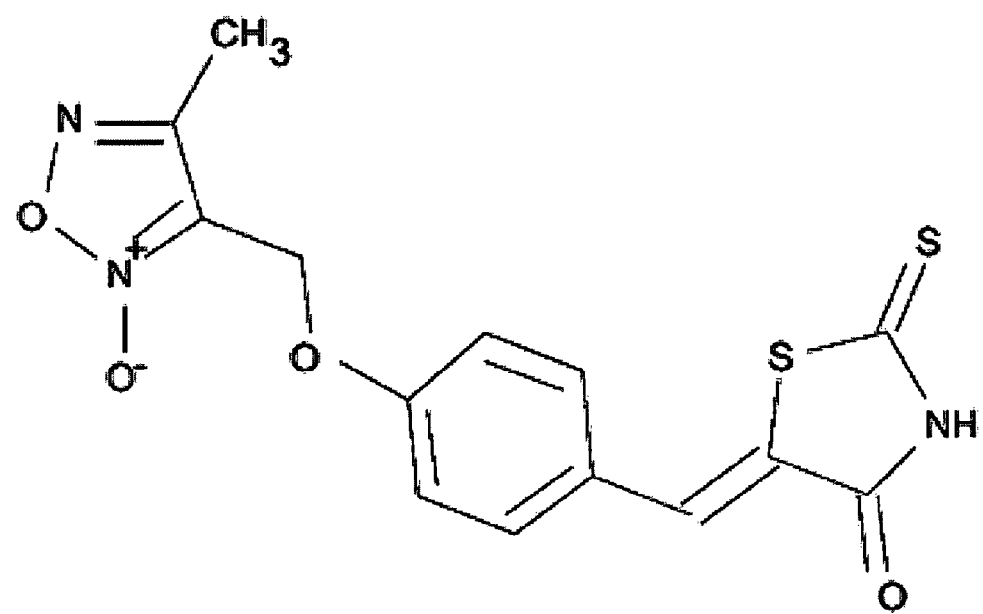
Figure 9J:
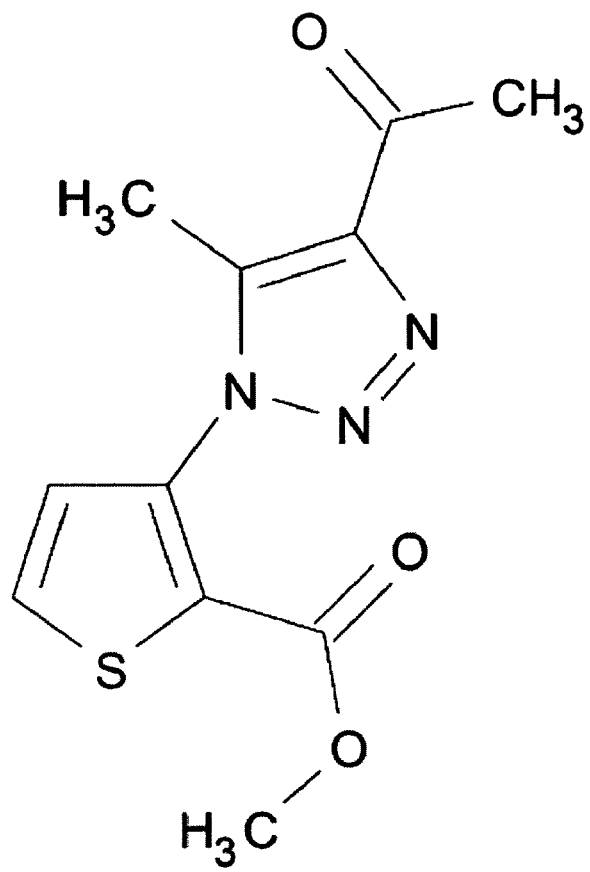
Figure 9J:
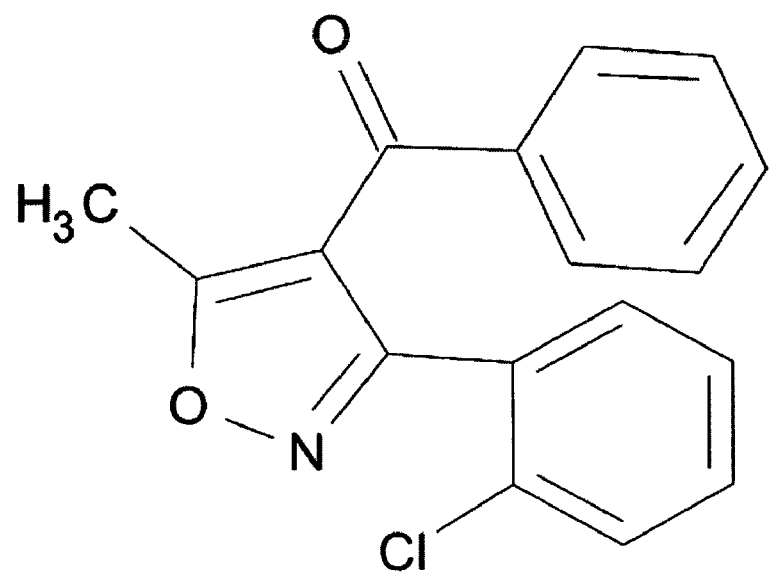

The inhibition of compound 738 on sperm hyperactivation was studied in more detail. Compound 738 inhibits sperm hyperactivation in a dose-dependent manner (FIG. 5). The $IC_{50}$ of 738 for inhibiting sperm hyperactivation was determined to be 40 μM in a dose response curve (FIG. 6). The Structure of 738 is shown in FIG. 8, top panel.

Example 4

Compound 354 Profoundly and Specifically Inhibits Hyperactivation

Figure 7:
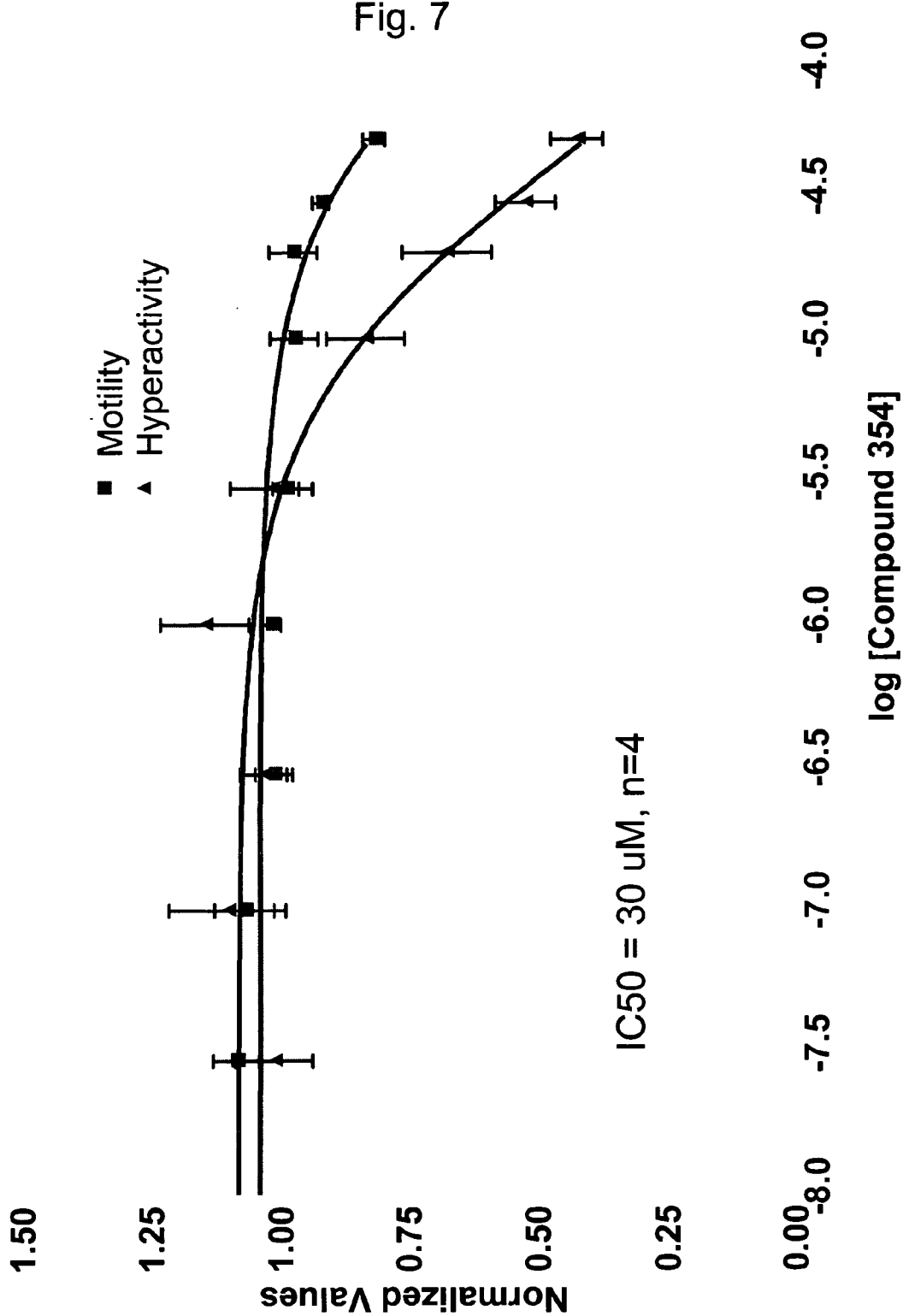
FIG. 7 shows a dose response of sperm hyperactivity to compound 354.

The inhibition of compound 354 on sperm hyperactivity was also determined. In a dose response study, the $IC_{50}$ of 354 was determined to be 30 μM (See FIG. 7). The Structure of 354 is shown on the bottom panel FIG. 8.

Example 5

Design and Testing of Additional Compounds Based on the Structures of Compounds 738 and 354

Figure 10:
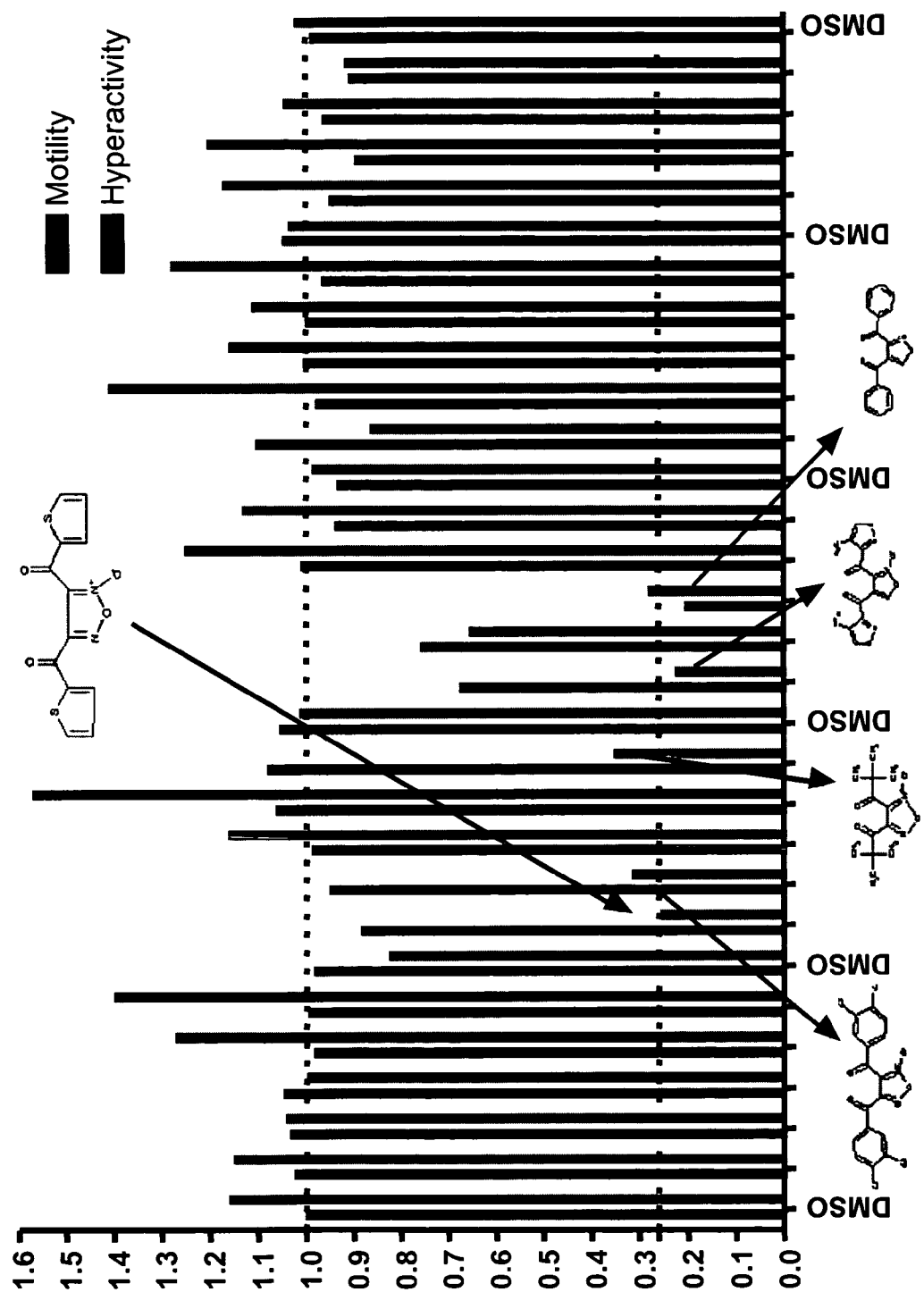
FIG. 10 shows representative testing of compounds for specific inhibition of sperm hyperactivation.
Figure 11:
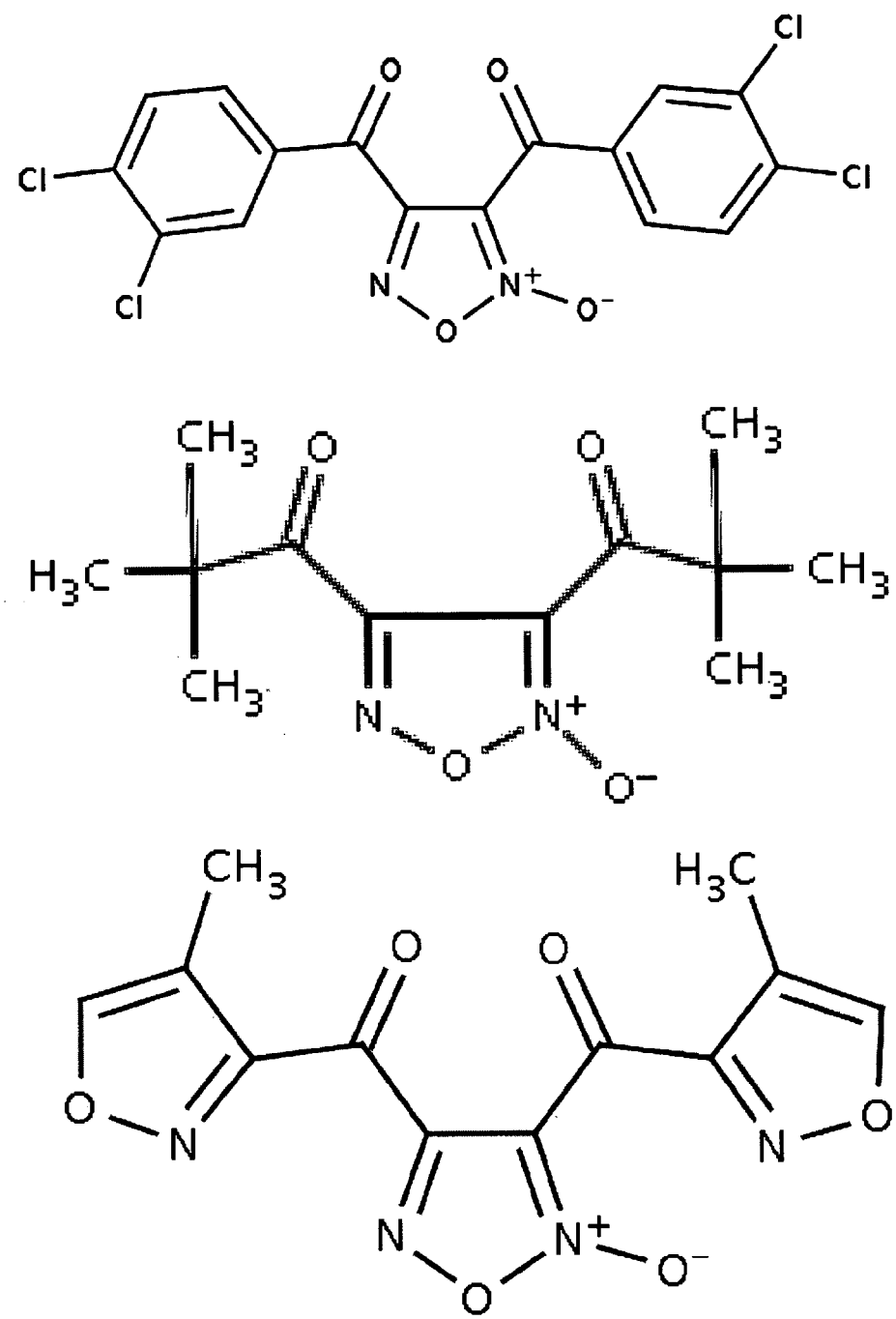
FIG. 11 shows three compounds found to specifically inhibit sperm hyperactivation.

Additional compounds related to 738 and 354 were tested for specific inhibition of sperm hyperactivity. FIG. 9 shows the formulas of the compounds that were tested. FIG. 10 shows representative results of compounds tested for specific inhibition of sperm hyperactivation. Three compounds were found to specifically inhibit sperm hyperactivation. Their structures are shown on FIG. 11.

Example 6

Figure 12:
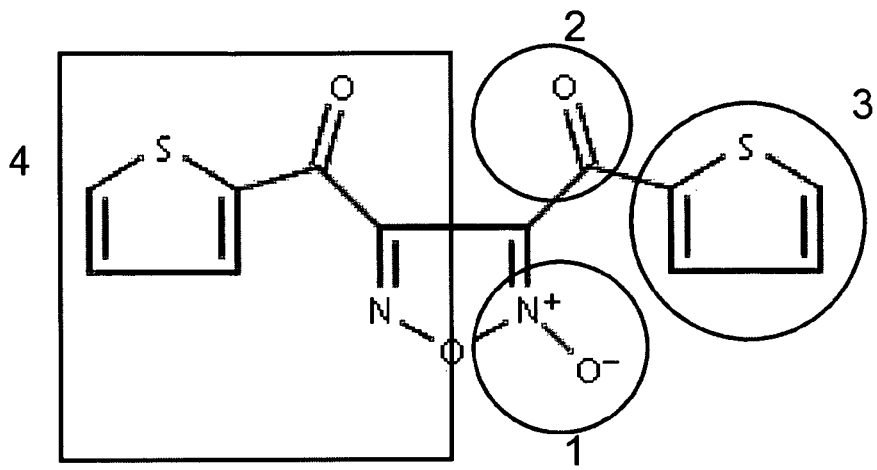
FIG. 12 shows a diagram of the structural elements found to be important for inhibiting sperm hyperactivation.
Figure 13:
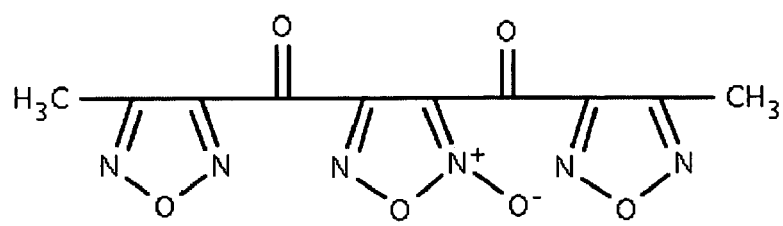
FIG. 13 shows the importance of the flat planar (Thiophene/Phenyl) moiety for specific inhibition of sperm hyperactivity.
Figure 13:
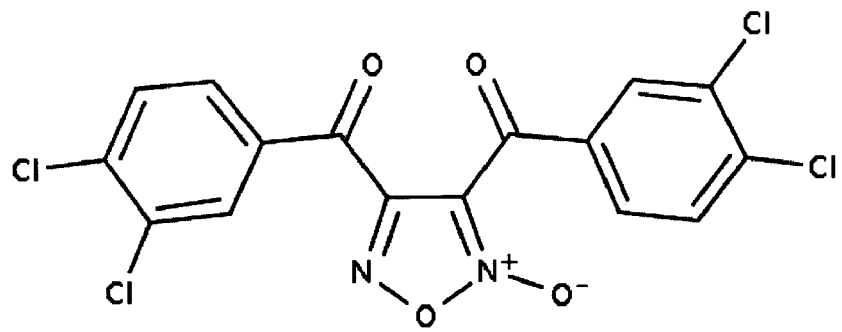
Figure 13:
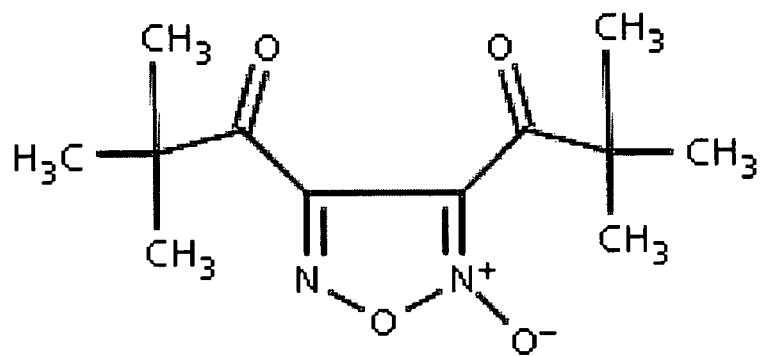
Figure 14:
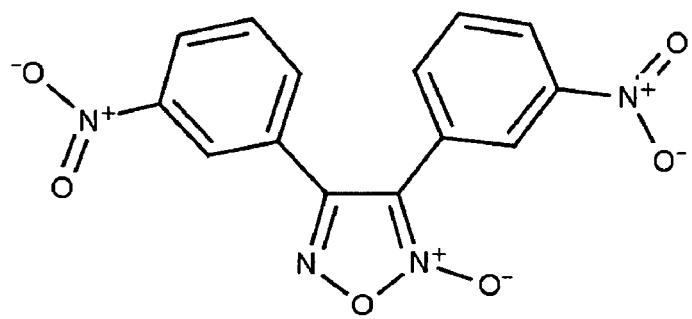
FIG. 14 shows the importance the carbonyl oxygen for specific inhibition of sperm hyperactivity.
Figure 14:
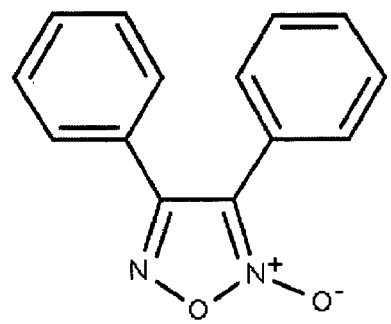
Figure 14:
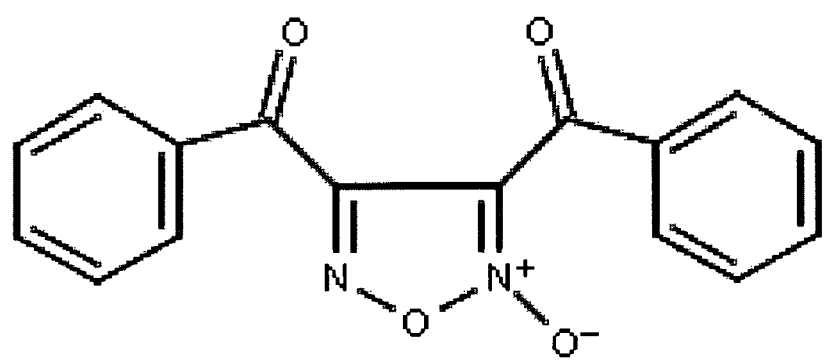
Figure 15:
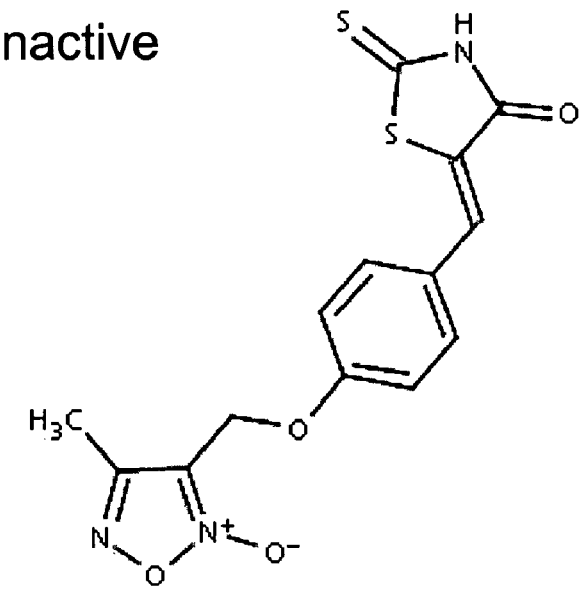
FIG. 15 shows the importance of symmetry for specific inhibition of sperm hyperactivity.
Figure 15:
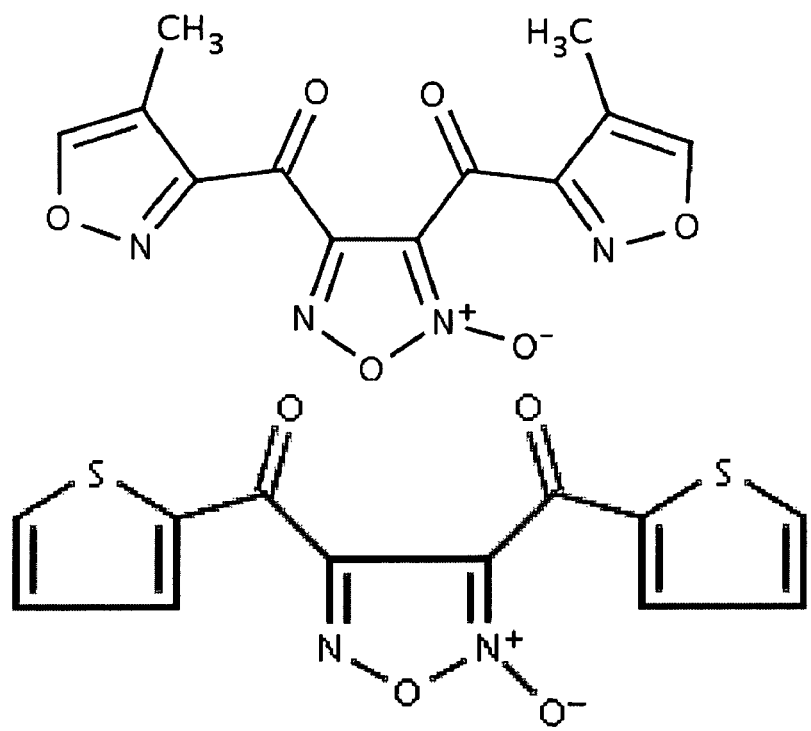
Figure 16:
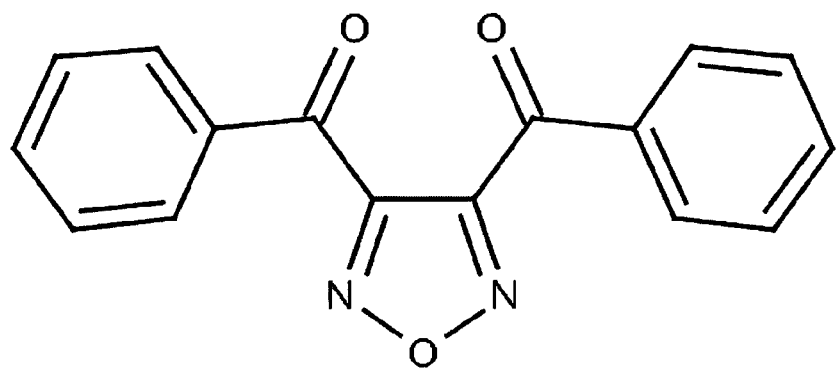
FIG. 16 shows the importance of the charged N+—O— moiety for specific inhibition of sperm hyperactivity (top panel).
Figure 16:
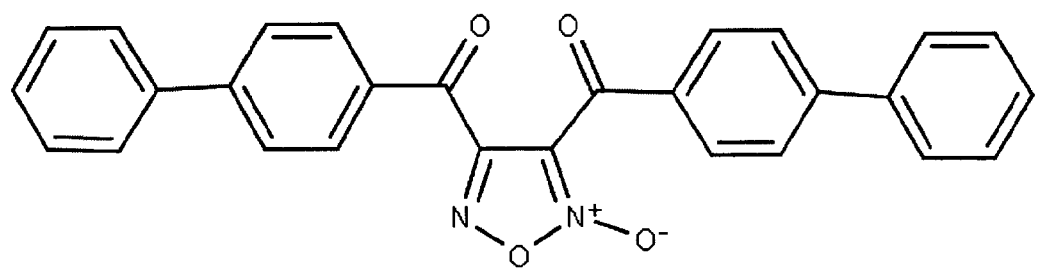

Elucidation of Structural Features for Specific Inhibition of Sperm Hyperactivation Based on which compounds that were active and inactive, four features were determined to be important for specific inhibition of sperm hyperactivity. These are shown in FIG. 12 and are as follows: (a) permanently charged N—O group; (b) carbonyl oxygen; (c) large planar group; and (d) bilateral symmetry. Additional compounds were tested in support of the importance of these features and are shown in FIGS. 13-16. The bottom panel of FIG. 16 shows an additional compound found to be inactive.

Example 7

Testing CatSper1 inhibitors in a Single Sperm Motility Assay

Compounds represented by structures (II)-(VI) are tested for their effects on sperm hyperactivation using a single-sperm motility assay as described in Carlson et al., (2003) *PNAS* 100(25), p. 14864. Sperm are washed twice and then dispersed and stored at 1-2×107 cells per ml. Potassium-evoked responses are produced with medium K8.6 (in mM): 135 KCl, 5 NaCl, 2 CaCl2, 1 Mg SO4, 30 TAPS [N-tris (hydroxymethyl)-methyl-3-aminopropanesulfonic acid], 10 glucose, 10 lactic acid, 1 pyruvic acid, adjusted to pH 8.6 with NaOH. For incubation under capacitating conditions, stored sperm are sedimented and resuspended in the original volume of warmed swimout/capacitation medium. After 90 min at 37° C. with 5% CO2, cells are again sedimented and returned to medium Na7.4 with or without added 15 mM NaHCO3. For dye loading and photometry, Indo-1 acetoxymethyl ester (AM) is dispensed from a 2 mM stocks in DMSO, dispersed in 10-15% Pluronic 127, diluted to 20 μM in 0.25 ml medium Na7.4, and then immediately mixed with an equal volume of the sperm suspension. After 15-20 min, cells are diluted in 1 ml of medium Na7.4, sedimented, and then resuspended in fresh medium and incubated for 1-5 h before use. Cells (10 μl) are applied and allowed to settle for ~5 min on ~5-mm-square no. 00 coverslips. A local perfusion device with an estimated exchange time of <0.5 s applies various test solutions. Photometric measurements are made as described (Wennemuth et al. (2000) *J. Biol. Chem.* 275, 21210-21217; Wennemuth et al. (2003) *Development* 130, 1317-1326) and analyzed in Igor (Wavemetrics, Lake Oswego, Oreg.). Statistical analyses are performed in EXCEL (Microsoft, Redmond, Wash.). AU results are presented as mean±SEM except as noted.

For permeant Ester Loading of cAMP, cAMP-AM is dispensed from a 20 mM stock in DMSO, dispersed in 10-15% Pluronic 127, diluted to 120 μM in 0.25 ml of medium Na7.4, and then immediately mixed with an equal volume of a sperm suspension that had or had not received preliminary loading with indo-1 AM. After 30 min, an aliquot (5-10 μL) is added to the sample chamber for imaging. Cells are examined with protocols that minimized the duration of perfusion to thereby reduce washout of the membrane-permeant ester (Schultz et al. (1994) Mol. Pharmacol. 46, 702-728.) Images for waveform analysis are collected as described (Wennemuth et al. (2003) *Development* 130, 1317-1326.). Briefly, cells are examined with a ×40, 0.65 numerical aperture objective on an inverted microscope (Nikon Diaphot). Brief flashes (1-2 ms) of illuminating light, produced by a custom-built stroboscopic power supply, are triggered once-per-frame by a synchronization signal from the controller module of the frame-transfer cooled charge-coupled device camera (TCP512; Roper Scientific, Trenton, N.J.). Images are collected at 30 Hz from a 128_128-pixel region of the camera chip, under the direction of METAMORPH (Universal Imaging, Downington, Pa.) and stored in TIFF format. Subsequent analysis used software routines written in IGOR (Wavemetrics, Lake Oswego, Oreg.) that provided flagellar beat frequency and amplitude, and evaluated the angular deviation (tangent angle) at 0.5-μm intervals along the length of the traced flagellum (arc length). The time-averaged tangent angle vs. length-along-the-flagellum data (shear curves) provides a measure of flagellar beat asymmetry (2); for a general discussion of polymer mechanics and its analysis, see Howard, J. (2001) Mechanics of Motor Proteins and the Cytoskeleton (Sinauer,
Sunderland M A), pp. 99-116.

When the sperm are treated with increasing concentrations of compounds (II) to (VI), sperm hyperactivation decreases with increasing dosages of the compounds.

Example 8

Inhibition of CatSper1 Currents

Compounds represented by structures (II)-(VI) are tested for their effects on Ca+2 currents in single spermatozoa as described in Kirichok Y, Navarro B, Clapham D E. Whole-cell patch-clamp measurements of spermatozoa reveal an alkaline-activated Ca2+ channel. *Nature*. 2006 Feb. 9;439 (7077):737-40. Using this assay, increasing concentrations of compounds (II)-(VI) are shown to decrease Ca+2 currents in wild-type sperm. These compounds, however, have little of no effect on Ca+2 currents from CatSper1−/−sperm.

Example 9

In vivo Inhibition of Fertility in Mice Treated with Compounds (II)-(VI)

Compounds represented by structures (II)-(VI) are tested for their effects on male and female fertility. C57BL/6 mice are housed under standard nonsterile conditions. The mice are provided with water ad libitum and are fed pelleted chow (expanded Rat and Mouse Chow 3, SDS, Witham, Essex, U.K.) before drug administration. To administer each of the compounds, the mice are fed a diet of powdered mouse chow (expanded Rat and Mouse Chow 1, ground, SDS) containing either one of the five compounds, and a set of control animals receive no compound. The diet and compound (both as dry solids) are mixed thoroughly, stored at room temperature, and used within 7 days of mixing. Six-week-old male C57BL/6 mice are caged with four untreated female C57BL/6 mice, and provided with standard pelleted chow. Females are at least 11 weeks old, and age-matched in each experiment. The male is removed from the females after 7 or 9 days, depending on the experiment; the females are monitored for vaginal mucous plugs, pregnancies, and, if any, litter sizes. To study any effect on female fertility, six-week-old female C57BL/6 mice are treated with each of five compounds, or with no compound, for 5 weeks, after which each of them is caged with a nontreated age-matched male for 4 days.

Male mice treated with each of the five compounds show a concentration dependent drop in fertility compared with untreated mice. Likewise, female mice fed with each of the five compounds show a statistically-significant decrease in fertility compared with untreated females. The drop in fertility is reflected in a decrease in the overall number of pregnancies as well as on reduced litter sizes. Prolonged intake of the five compounds does not affect reproductive hormone levels, serum biochemistry or animal behavior in males and females.

Example 10

Reversible In vivo Inhibition of Fertility in Mice Treated with Compounds (II)-(VI)

Mice are treated as in example 9, except that oral administration of the compound is ceased after two months. The fertility of both female and male mice is monitored for the following six months. Both male and female mice regain normal fertility levels in a time-dependent fashion.

Example 11

Inhibition of Mouse CatSper1 Currents by Compound II in Electrophysiological Recordings Compound (II) was tested for its effects on sperm hyperactivation using a single-sperm motility assay as described in Kirichok Y, Navarro B, Clapham D E. "Whole-cell patch-clamp measurements of spermatozoa reveal an alkaline-activated Ca2+ channel". *Nature*. 2006;439(7077):737-40. Mouse sperm was prepared as described in Kirichok.

The patch pipette was applied to the sperm cell cytoplasmic droplet (CD). Spermatozoa from corpus epididymis were used because the CD of such cells was less fragile. The most mature spermatozoa, those with the CD located next to the principal piece, were chosen for experiments. Pipette resistance with Cs-Methanesulfonate-based solutions was 6-13 MΩ. Access resistance in the whole-cell configuration was 25-120 MΩ. The pipette solution (in mM) was as follows: 140 Cs-Methanesulfonate, 5 NaCl, 10 HEPES, 10 EGTA, pH 7.2 (pH adjusted with CsOH).

Seals between the patch pipette and the cytoplasmic droplet were formed in HS bath solution (Kirichok Y, Navarro B, Clapham D E. Whole-cell patch-clamp measurements of spermatozoa reveal an alkaline-activated Ca2+ channel. Nature. 2006 Feb. 9;439(7077):737-40). After break-in, the bath solution was changed to recording solution: 150 NaGluconate, 10 HEPES, 2Na3HEDTA and 2 EGTA, pH 7.4 (pH adjusted with NaOH). $CaCl_2$ was added to the solution in accordance with the WinMAXC v2.05 program (C. Patton, Stanford University) to yield ~2 micromolar free [Ca2+].

A 20 micromolar solution of compound (II), i.e. 3,4-bis(2-thienylcarbonyl)-1,2,5-oxadiazole-2-ium-2-olate, was prepared from a 100 mM DMSO stock in the recording solution described above. Osmolarity of the solutions was approximately 303 mmol kg-1.

The membrane potential was held at 0 mV. Every 5 seconds CatSper currents were monitored by application of a voltage ramp from −100 mV to +100 mV over the course of 400 milliseconds. Following break-in, cells were monitored until a steady state level of CatSper current (plotted at +80 mV) was observed. Compound II was applied and the current was monitored until a steady state block was achieved (usually 2-3 sweeps). Steady state block was monitored for 5-6 sweeps. Following removal of the compound the CatSper current returned rapidly to unblocked levels. Signals were sampled at 10 kHz, and filtered at 2.9 kHz. Series resistance was monitored throughout the recordings.

Compounds (I) and (II)-(VI) are similarly tested in this assay. Compounds (I) and (II)-(VI) are expected to cause a steady state block in CatSper currents in a concentration dependent manner.

We claim:

1. A method of selectively decreasing the hyperactivity of a spermatozoon, the method comprising contacting the spermatozoon with a compound selected from the group consisting of:

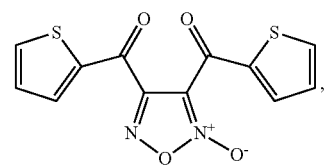

(II)

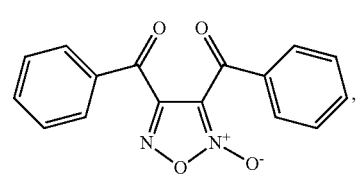

(III)

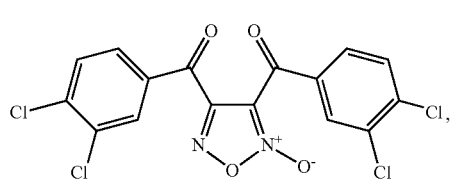

(IV)

-continued
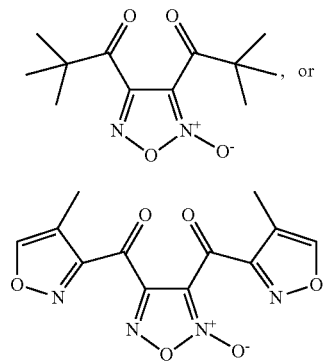
or a pharmaceutically acceptable salt thereof.
2. The method according to claim 1, wherein the compound is
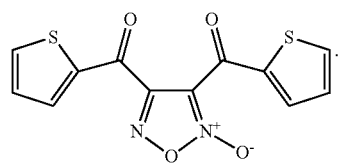
3. The method according to claim 1, wherein the compound is
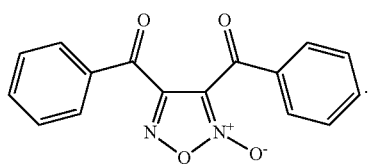
4. The method according to claim 1, wherein the compound is
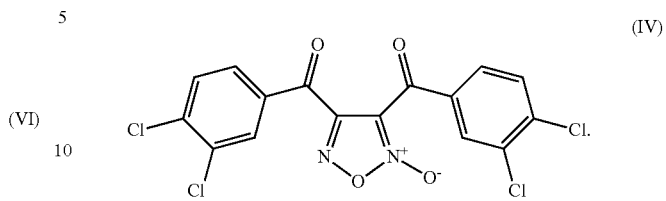
5. The method according to claim 1, wherein the compound is
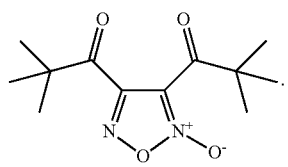
6. The method according to claim 1, wherein the compound is
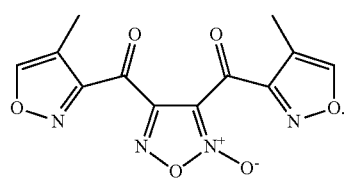
* * * * *